US011338025B2

(12) United States Patent
Peoples

(10) Patent No.: US 11,338,025 B2
(45) Date of Patent: May 24, 2022

(54) VACCINE THERAPY FOR TREATMENT OF ENDOMETRIAL AND OVARIAN CANCER

(71) Applicant: The Henry M. Jackson Foundation for the Advancement of Military Medicine, Inc., Bethesda, MD (US)

(72) Inventor: George E. Peoples, Spring Branch, TX (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 251 days.

(21) Appl. No.: 15/872,626

(22) Filed: Jan. 16, 2018

(65) Prior Publication Data

US 2018/0256692 A1   Sep. 13, 2018

Related U.S. Application Data

(63) Continuation of application No. 15/609,709, filed on May 31, 2017, now abandoned.

(60) Provisional application No. 62/343,675, filed on May 31, 2016.

(51) Int. Cl.
| | |
|---|---|
| *A61K 39/00* | (2006.01) |
| *A61K 39/39* | (2006.01) |
| *A61P 35/00* | (2006.01) |
| *A61K 9/00* | (2006.01) |

(52) U.S. Cl.
CPC ........ *A61K 39/0011* (2013.01); *A61K 9/0019* (2013.01); *A61K 39/39* (2013.01); *A61P 35/00* (2018.01); *A61K 2039/545* (2013.01); *A61K 2039/55516* (2013.01); *A61K 2039/55522* (2013.01); *A61K 2039/585* (2013.01)

(58) Field of Classification Search
CPC ....... A61K 39/0011; A61K 38/08; C07K 7/06
See application file for complete search history.

(56) References Cited

U.S. PATENT DOCUMENTS

| | | | |
|---|---|---|---|
| 5,803,755 | A | 9/1998 | Kuchar et al. |
| 5,846,538 | A | 12/1998 | Cheever et al. |
| 6,153,430 | A | 11/2000 | Pastan et al. |
| 6,514,942 | B1 | 2/2003 | Ioannides et al. |
| 7,547,759 | B2 | 6/2009 | Ioannides et al. |
| 8,258,261 | B2 | 9/2012 | Ioannides et al. |
| 8,470,822 | B2 | 6/2013 | Green et al. |
| 8,815,256 | B2 | 8/2014 | Ioannides et al. |
| 9,562,070 | B2 | 2/2017 | Ioannides et al. |
| 9,993,538 | B2 | 6/2018 | Peoples |
| 2003/0027766 | A1 | 2/2003 | Ioannides et al. |
| 2003/0077248 | A1 | 4/2003 | Moriarty et al. |
| 2003/0185840 | A1 | 10/2003 | Ioannides et al. |
| 2010/0209443 | A1 | 8/2010 | Peoples et al. |
| 2015/0175658 | A1 | 6/2015 | Ioannides et al. |
| 2017/0007687 | A1 | 1/2017 | Peoples |
| 2018/0194806 | A1 | 7/2018 | Ioannides et al. |
| 2019/0117749 | A1 | 4/2019 | Peoples |

FOREIGN PATENT DOCUMENTS

| | | |
|---|---|---|
| WO | 02/072766 A2 | 9/2002 |
| WO | 2007/143561 A1 | 12/2007 |
| WO | 2016/196506 A1 | 12/2016 |

OTHER PUBLICATIONS

Kiecker et al., Human Immunology, 2004, 65: 523-536.*
Clinical Trial NCT01580696 version 4, posted on Aug. 18, 2014.*
Clinical Trial NCT02019524 version 1, posted on Dec. 18, 2013.*
Benavides et al., Clin. Cancer Res., 2009, 15(8); 2895-2904.*
Markert et al., Anticancer Research, 2008, 28:3567-3752.*
Greene et al., Preliminary results of the Phase IIa trial ofa folate binding protein (FBP) adjuvant cancer vaccine (E39+GM-CSF) in ovarian and endometrial cancer patients to prevent recurrence, Journal of ImmunoTherapy of Cancer, Nov. 6, 2014, 2(suppl.3) Abstract P74.*
Abrams, Scott et al., "Rational Antigen Modification as a Strategy to Upregulate or Downregulate Antigen Recognition," Immunology, vol. 12:85-91 (2000).
Alexander, Richard B. et al., "Adoptively Transferred Tumor-Infiltrating Lymphocytes Can Cure Established Metastatic Tumor in Mice and Persist Long-Term In Vivo as Functional Memory T. Lymphocytes," Journal of Immunotherapy, vol. 10:389-397 (1991).
Allard, JE et al., "Overexpression of folate binding protein is associated with shortened progression-free survival in uterine adenocarcinomas," Gynecol Oncol., vol. 107:52-57 (2007).
Andersen, M.H. et al., "Poor correspondence between predicted and experimental binding of peptides to class I MHC molecules," Tissue Antigens, vol. 55:519-531 (2000).
Antony, AC., "The biological chemistry of folate receptors," Blood, vol. 79:2807-2820 (1992).
Bast R.C. Jr. et al., "A radioimmunoassay using a monoclonal antibody to monitor the course of epithelial ovarian cancer," N Engl J Med., vol. 309:883-887 (1983).
Bednarek, Maria A. et al., "Soluble HLA-A2.1 restricted peptides that are recognized by influenza virus specific cytotoxic T lymphocytes," Journal of Immunological Methods, vol. 139:41-47 (1991).
Bodey, B. et al., "Failure of cancer vaccines: the significant limitations of this approach to immunotherapy," Anticancer Res., vol. 20(4):2665-2676 (2000).
Bon, G.C. et al., "Serum tumor marker immunoassays in gynecologic oncology: establishment of reference values," Am J Obstet. Gynecol., vol. 174:107-114 (1996).

(Continued)

*Primary Examiner* — Hong Sang
(74) *Attorney, Agent, or Firm* — MH2 Technology Law Group, LLP

(57) ABSTRACT

The present invention provides methods of preventing or reducing the risk of recurrence of endometrial and ovarian cancers which express low levels of folate binding protein (FBP) by administration of a vaccine containing an E39 peptide.

22 Claims, 10 Drawing Sheets

Specification includes a Sequence Listing.

(56) References Cited

OTHER PUBLICATIONS

Boon, Thiery, "Toward a Genetic Analysis of Tumor Rejection Antigens," Advances in Cancer Research, vol. 58:177-210 (1992).
Bottero, F et al., "Gene transfection and expression of the ovarian carcinoma marker folate binding protein on NIH/3T3 cells increases cell growth in vitro and in vivo," Cancer Res vol. 53:5791-5796 (1993).
Bowie, James U. et al., "Deciphering the Message in Protein Sequences: Tolerance to Amino Acid Substitutions," Science, vol. 247:1306-1310 (1990).
Buelow, Roland et al., "Localization of the immunologic activity in the recognized by staphylococcal enterotoxin B using truncated recombinant fusion proteins," The Journal of Immunology, vol. 148(1):1-6 (1992).
Campbell, I.G. et al., "Folate-binding protein is a marker for ovarian cancer," Cancer Research, vol. 51(19):5329-5338 (1991).
Castille J.A. Agapito et al., "Induction of Tumor-Reactive CTL by C-Side Chain Variants of the CTL Epitope HER-2/neu Protooncogene (369-377) Selected by Molecular Modeling of the Peptide: HLA-A2 Comples," The Journal of Immunology, vol. 169(7):3545-3554 (2002).
Chancy, CD et al., "Expression and differential polarization of the reduced-folate transporter-1 and the folate receptor alpha in mammalian retinal pigment epithelium," J. Biol Chem., vol. 275:20676-20684 (2000).
Chianese-Bullock, KA et al., "A multipeptide vaccine is safe and elicits T-cell responses in participants with advanced stage ovarian cancer.," J Immunother., vol. 31:420-430 (2008).
Clifton et al.,"Folate receptor ?: a storied past and promising future in immunotherapy," Human Vaccines, vol. 7(2):183-190(2011).
Cohen, JG et al., "In 2014, can we do better than CA125 in the early detection of ovarian cancer?," World J. Chem., vol. 5(3):286-300 (2014).
Crane, L. et al, "The effect of chemotherapy on expression of folate receptor-alpha in ovarian cancer," Cellular Oncology, vol. 35(1):9-18 (2012).
Dalgleish, AG, "Cancer vaccines," British Journal of Cancer, vol. 82(10):1619-1624 (2000).
Deplaen, E. et al., "Structure, chromosomal localization, and expression of 12 genes of the MAGE family," Immunogenetics, vol. 40(5):360-369 (1994).
European Search Report for Application No. 11004714.9, 6 pages, dated Nov. 21, 2011.
Ezzell, "Cancer 'Vaccines': An Idea Whose Time Has Come?" The Journal of NIH Research, vol. 7:46-49 (1995).
Falk, Kirsten et al., "Allele-specific motifs revealed by sequencing of self-peptides eluted from MHC molecules," Nature, vol. 351:290-296 (1991).
Feltkamp, Mariet C.W. et al., "Efficient MHC Class I-Peptide Binding is Required but Does Not Ensure MHC Class I-Restricted Immunogenicity," Molecular Immunology, vol. 31(18):1391-1401 (1994).
Fisk, B. et al., "Changes in an HER-2 peptide upregulating HLA-A2 expression affect both conformational epitopes and CTL recognition: implications for optimization of antigen presentation and tumor-specific CTL induction," J. Immunother. Emphasis Tumor Immunol., vol. 18(4):197-209 (1995).
Forni, G. et al., "Immunization in tumor prevention," Int. Immunopharmacol., vol. 3(8):1151-1158 (2003).
Gao, P. et al., "Tumor vaccination that enhances antitumor T-cell responses does not inhibit the growth of established tumors even in combination with interleukin-12 treatment: the importance of inducing intratumoral T-cell migration," J. Immunother., vol. 23(6):643-653 (2000).
Greenspan, N.S. et al., "Defining epitopes: It's not as easy as it seems," Nat. Biotechnol., vol. 17(10):936-937 (1999).
Guichard, Gilles et al., "Melanoma Peptide MART-1(27-35) Analogues with Enhanced Binding Capacity to the Human Class I Histocompatibility Molecule HLA-A2 by Introduction of a beta-Amino Acid Residue: Implications for Recognition by Tumor-Infiltrating Lymphocytes," J. Med. Chem., vol. 43:3803-3808 (2000).
Gura, T., "Systems for identifying new drugs are often faulty," Science, vol. 278(5340):1041-1042 (1997).
Hartmann, LC., "Folate receptor overexpression is associated with poor outcome in breast cancer," Int J Cancer, vol. 121:938-942 (2007).
Hernando et al. "Vaccination with dendritic cells transfected with mRNA-encoded folate-receptor-a for relapsed metastatic ovarian cancer," The Lancet Oncology, ; vol. 8 (5): 451-454 (2007).
Holmes, E.H., "PSMA specific antibodies and their diagnostic and therapeutic use," Expert Opin. Investig. Drugs, vol. 10(3):511-519 (2001).
Huard, R. et al., "The critical role of a solvent-exposed residue of an MHC class I-restricted peptide in MHC-peptide binding," Int. Immunol., vol. 9(11):1701-1707 (1997).
Hudson, J. et al., "Growth and Antigen Recognition of Tumor-Infiltrating Lymphocytes from Human Breast Cancer," Journal of Interferon and Cytokine Research, vol. 18:529-536 (1998).
International Preliminary Report on Patentability, PCT/US2017/035133, dated Dec. 4, 2018, 8 pages.
International Search Report and Written Opinion, PCT/US2016/035086, dated Sep. 29, 2016, 6 pages.
International Search Report and Written Opinion, PCT/US2017/035133, dated Sep. 8, 2017, 16 pages.
Ioannides, Constantin G. et al., "Cytokine T Cell Clones Isolated From Ovarian Tumor-Infiltrating Lymphocytes Recognize Multiple Antigenic Epitopes on Autologous Tumor Cells," The Journal of Immunology, vol. 146(5):1700-1707 (1991).
Ioannides, Constantin G. et al., "Cytotoxic T Cells Isolated from Ovarian Malignant Ascites Recognize a Peptide Derived from the HER-2/neu Proto-oncognee," Cellular Immunology, vol. 151:225-234 (1993).
Ioannides, Constantin G. et al., "T-Cell Recognition on Oncogene Products: A New Strategy for Immunology," Molecular Carcinogenesis, vol. 6:77-82 (1992).
Ioannides, Constantin G., "Clarification of the Functional Significance of Human Folate-binding Protein-Peptide, 191-199, based on a Correct GenBank Sequence and on Other FBP (191-199) Sequences," Anticancer Res., vol. 27(4B):2251-2252 (2007).
Ioannides, Constantin G., "Cytotoxic T Cells from Ovarian Malignant Tumors Can Recognize Polymorphic Epithelial Mucin Core Peptides," The Journal of Immunology, vol. 151(7):3693-3703 (1993).
Ioannides, Constantin G., "Induction of Interleukin-2 receptor by tumor necrosis factor a on cultured ovarian tumor-associated lymphocites," Cancer Immunol. Immunother., vol. 35:83-91 (1992).
Ioannides, Constantin G., "Lymphocytes Infiltrating Ovarian Malignant Ascites: Modulation of IL-2-induced Proliferation by IL-4 and of Selective Increase in CD8+ T Cells by TNF-alpha," Lymphokine and Cytokine Research, vol. 10(4):307-315 (1991).
Jackson et al. "P156: Preliminary report of a clinical trial supporting the sequential use of an attenuated E39 peptide (E39') to optimize the immunologic response to the FBP (E39+GM-CSF) vaccine," Journal for Immuno Therapy of Cancer, vol. 3(Supp. 2): 1-2, 2015.
Jackson, D. et al., "Interim analysis of a phase I/IIa trial assessing E39+GM-CSF, a folate binding protein vaccine, to prevent recurrence in ovarian and endometrial cancer patients," Oncotarget, vol. 8(9):15912-15923 (2017).
Kim, DK et al., "Folate binding protein peptide 191-199 presented on dendritic cells can stimulate CTL from ovarian and breast cancer patients," Anticancer Res., vol. 19:2907-2916 (1999).
Kim, Dong-Kyu et al., "The Comparison of Cytotoxic T-Lymphocyte Effects of Dendritic Cells Stimulated by the Folate Binding Protein Peptide Cultured with IL-15 and IL-2 in Solid Tumor," Yonsei Medical Journal, vol. 43(6):691-700 (2002).
Knutson, KL, et al., "T-cell immunity to the folate receptor alpha is prevalent in women with breast or ovarian cancer," J Clin Oncol., vol. 24:4254-4261 (2006).
Kos, Ferdynand J. et al., "Specific epitope-induced conversion of CD8+ memory cells into effector cytotoxic T lymphocytes in vitro: presentation of peptide antigen by CD8+ T cells," Eur. J. Immunol., vol. 22:1595-1601 (1992).

(56) References Cited

OTHER PUBLICATIONS

Lee, K.H. et al., "Increased vaccine-specific T cell frequency after peptide-based vaccination correlates with increased susceptibility to in vitro stimulation but does not lead to tumor regression," J. Immunol., vol. 163(11):6292-6300 (1999).
Lee, TV et al., "Identification of activated tumor antigen-reactive CD8+ cells in healthy individuals," Oncol Rep., vol. 7:455-466 (2000).
Leung, F et al., "Folate-receptor 1 (FOLR1) protein is elevated in the serum of ovarian cancer patients," Clin. Biochem, vol. 46:1462-1468 (2013).
Li, Peng Young et al., "Local Concentration of Folate Binding Protein GP38 in Sections of Human Ovarian Carcinoma by In Vitro Quantitative Autoradiography," J. Nucl. Med., vol. 37:665-672 (1996).
Liu, J. et al., "Targeted drug delivery to chemoresistant cells: folic acid derivatization of FdUMP[10] enhances cytotoxicity toward 5-FU-resistant human colorectal tumor cells," J Org Chem., vol. 66:5655-5663 (2001).
Lollini, P.L. et al., "Cancer immunoprevention: tracking down persistent tumor antigens," Trends Immunol., vol. 24(2):62-66 (2003).
Lu, Y. et al., "Immunotherapy of folate receptor-expressing tumors: review of recent advances and future prospects," J. Control Release, vol. 91(1-2):17-29 (2003).
Mantovani, L.T. et al., "Folate Binding Protein Distribution in Normal Tissues and Biological Fluids From Ovarian Carcinoma Patients as Detected by the Monoclonal Antibodies MOv18 and MOv19," European Journal of Cancer, vol. 30A(3):363-369 (1994).
Markert, S. et al., "Alpha-folate receptor expression in epithelial ovarian carcinoma and non-neoplastic ovarian tissue," Anticancer Res., vol. 28:3567-3572 (2008).
Mazzoni, A. et al., "CD3-CD28 costimulation as a means to avoiding T cell preactivation in bispecific monoclonal antibody-based treatment of ovarian carcinoma," Cancer Res., vol. 56(23):5443-5449 (1996).
McCullough, K.C. et al., "Basic concepts of immune response and defense development," ILAR J., vol. 46(3):230-240 (2005).
Neglia et al. "DNA vaccination against the ovarian carcinoma-associated antigen folate; receptor u (FRu) induces cylotoxic T lymphocyte and antibody responses in mice," Cancer; Gene Therapy, vol. 6 (4): 349-357 (1999).
O'Shannessy, DJ et al., "Characterization of the human folate receptor alpha via novel antibody-based probes," Onco Target, vol. 2:1227-1243 (2011).
Pardoll, Drew M., "Therapeutic Vaccination for Cancer," Clinical Immunology, vol. 95(1):S44-S62 (2000).
Peoples, GE et al., "Vaccine implications of folate binding protein, a novel cytotoxic T lymphocyte-recognized antigen system in epithelial cancers," Clin Cancer Res., vol. 5:4214-4223 (1999).
Peoples, GE, et al."Ovarian cancer-associated lymphocyte recognition of folate binding protein peptides," Ann Surg Oncol., vol. 5:743-750 (1998).
Pietersz, G.A. et al., "Generation of Cellular Immune Responses to Antigenic Tumor Peptides," CMLS Cellular and Molecular Life Sciences, vol. 57:290-310 (2000).
Pillae et al., "Expression of folate receptors and heterogeneous nuclear ribonucleoprotein E1 in women with human papillomavirus mediated transformation of cervical tissue to cancer," J. Clin. Pathol., vol. 56:569-574 (2003).

Rosenberg, Steven A., "The Identification of Cancer Antigens: Impact on the Development of Cancer Vaccines," The Cancer Journal, vol. 6(Suppl. 2):S142-S149 (2000).
Ruppert, J. et al., "Prominent role of secondary anchor residues in peptide binding to HLA-A2.1 molecules," Cell, vol. 74(5):929-937 (1993).
Saijo, N., "What are the reasons for negative phase III trials of molecular-target-based drugs?" Cancer Science, vol. 95(10):772-776 (2004).
Sanchez-Del-Campo, L. et al., "The critical role of alpha-folate receptor in the resistance of melanoma to methotrexate," Pigment Cell Melanoma Res., vol. 22:588-600 (2009).
Schirle, Markus et al., "Combining computer algorithms with experimental approaches permits the rapid and accurate identification of T cell epitopes from defined antigens," Journal of Immunological Methods, vol. 257:1-16 (2001).
Shia, J. et al., "Immunohistochemical expression of folate receptor alpha in colorectal carcinoma: patterns and biological significance," Human Pathol., vol. 39:498-505 (2008).
Skolnick, J. et al., "From genes to protein structure and function: novel applications of computational approaches in the genomic era," Trends in Biotechnology, vol. 18(1):34-39 (2000).
Solanky et al.,"Expression of folate transporters in human placenta and implications for homocysteine metabolism," Placenta, vol. 31:134-143 (2010).
Spitler, L.E. et al., "Cancer vaccines: the interferon analogy," Cancer Biother., vol. 10(1):1-3 (1995).
Supplementary Partial European Search Report for Application No. 02750589.0, 5 pages, dated Jan. 29, 2008.
Toffoli et al., "Expression of folate binding protein as a prognostic factor for response to platinum-containing chemotherapy and survival in human ovarian cancer," Int J Cancer, vol. 79:121-126 (1998).
Toffoli et al., "Overexpression of folate binding protein in ovarian cancers," Int J Cancer vol. 74:193-198 (1997).
Valmori, D. et al., "Diversity of the fine specificity displayed by HLA-A 0201-restricted CTL specific for the immunodominant Melan-A/MART-1 antigenic peptide," J. Immunol., vol. 161(12):6956-6962 (1998).
Valmori, Danila et al., "Enhanced Generation of Specific Tumor-Reactive CTL In Vitro by Selected Melan-A/MART-1 Immunodominant Peptide Analogues," The Journal of Immunology, vol. 160:1750-1758 (1998).
Van Der Burg, Sjoerd H. et al., "Immunogenicity of Peptide Bound to MHC Class I Molecules Depends on the MHC-Peptide Complex Stability," The Journal of Immunology, vol. 156:3308-3314 (1996).
Weitman, SD et al., "Distribution of the folate receptor GP38 in normal and malignant cell lines and tissues," Cancer Res., vol. 52(12):3396-4401 (1992).
Yamshchikov, G. et al., "Analysis of a natural immune response against tumor antigens in a melanoma survivor: lessons applicable to clinical trial evaluations," Clin. Cancer Res., vol. 7(3 Suppl. ):909s-916s (2001).
Yu, K. et al., "Methods for prediction of peptide binding to MHC molecules: a comparative study," Mol. Med., vol. 8(3):137-148 (2002).
Zaks, T.Z. et al., "Immunization with a peptide epitope (p. 369-377) from HER-2/neu leads to peptide-specific cytotoxic T lymphocytes that fail to recognize HER-2/neu+ tumors," Cancer Res., vol. 58(21):4905-4908 (1998).

* cited by examiner

OVERALL CONTROL v. E39

Log Rank=0.172
Control n=22 (28.7%)
E39 n=29 (23.6%)
Median f/u=16.3 months

FOLATE EXPRESSION 0,1+ vs. 2-4+
A.
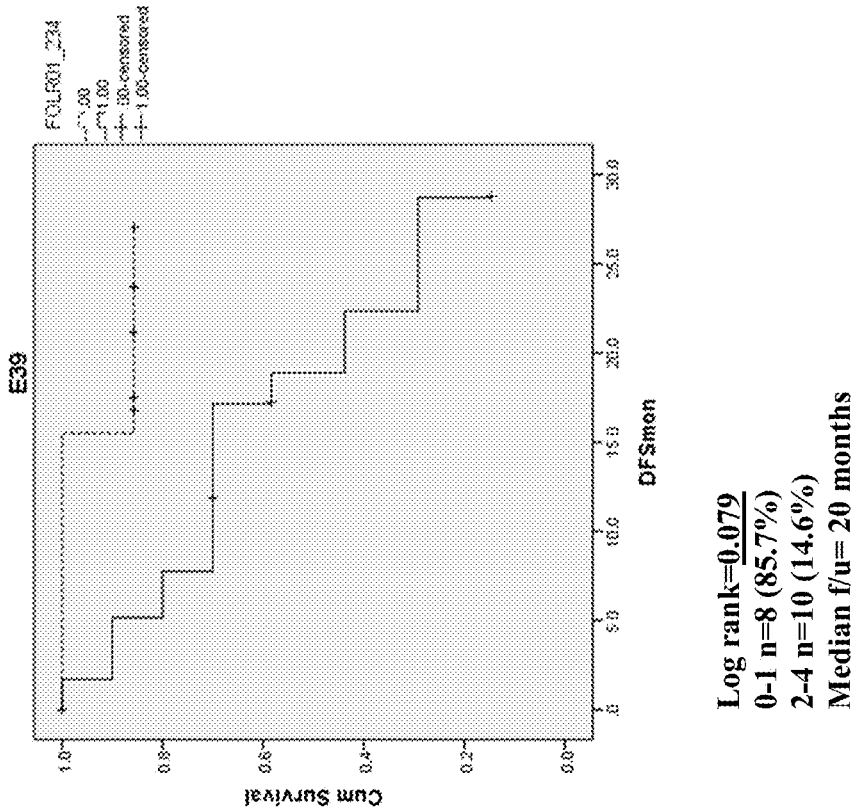
B.
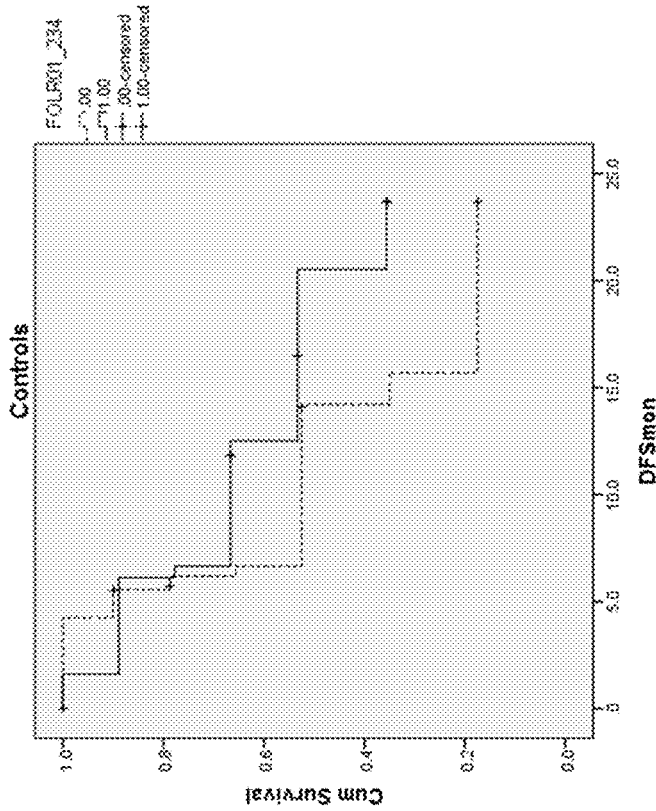
Log rank=0.441
0-1 n=11 (17.5%)
2-4 n=9 (35.6%)
Median f/u= 12.5 months
Log rank=0.079
0-1 n=8 (85.7%)
2-4 n=10 (14.6%)
Median f/u= 20 months
FIGURE 8

VACCINE THERAPY FOR TREATMENT OF ENDOMETRIAL AND OVARIAN CANCER

RELATED APPLICATIONS

This application is a continuation of U.S. patent application Ser. No. 15/609,709, which was filed May 31, 2017, which claims the benefit of the priority date of U.S. Provisional Application No. 62/343,675 which was filed May 31, 2016. The contents of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on May 31, 2018, is named RXJ-024CN_Sequence_Listing.txt and is 4,488 bytes in size.

FIELD OF THE INVENTION

The present invention is directed to the use of peptide based cancer vaccines.

BACKGROUND OF THE INVENTION

Endometrial cancer is the most common gynecologic cancer in the United States (Senol, et al., *Int. J. Clin. Exp. Pathol.* 2015; 8(5):5633-5641). Ovarian cancer, though less common, is the most common cause of death amongst gynecologic cancers. Due to the nonspecific symptoms of ovarian cancer, >70% of patients will present with late stage disease and, even with aggressive regimens, fewer than 40% of women with ovarian cancer are cured after standard of care treatment. Endometrial cancer has a much better prognosis in general because of earlier diagnosis, but even in early stage disease, 10-15% of patients will experience a recurrence. The serous variant of endometrial cancer is particularly aggressive, often presenting with evidence of metastasis (Black et al., *Int J of Gyn Cancer.* 2016; 26(1): 133-140), and having a clinical course more similar to that of ovarian carcinoma than typical endometrial cancer. Although only responsible for 3-10% of all endometrial cancers, this subtype leads to a high risk of recurrence, and up to 40% of endometrial cancer deaths.

Current treatments for endometrial and ovarian cancer include surgery, chemotherapy, and radiation, but these are insufficient in some patients, particularly those with unfavorable histology and advanced tumor stages. In addition, several novel medications have been tested in patients with Stage II or higher endometrial and ovarian cancers, including those that inhibit biochemical processes (anti-angiogenesis, DNA repair mechanisms, mTOR pathway, etc.) and monoclonal antibodies (anti-CA125 and anti-human epithelial cell adhesion molecule—EpCAM) (Ziebarth et al., Molecular/Genetic Therapies in Ovarian Cancer: Future Opportunities and Challenges. In: *Clinical Obstetrics and Gynecology.* 2012. Baltimore, Md.; Tse et al. *Ann Oncol* 2014; 25(2):322-331).

The folate binding protein (FBP), also known as folate receptor-alpha (FRα), is a tumor associated antigen (TAA) common to both endometrial and ovarian cancer with up to 80-90 fold higher expression in malignant cells compared to normal cells (Li et al., *J Nucl Med.* April 1996; 37(4):665-672; Weitman et al., *Cancer Res.* Jun. 15, 1992; 52(12): 3396-3401). FBP levels coincide with increased folate uptake, which is necessary for DNA production in rapidly replicating cells. As a result, its over-expression has been associated with higher grade and stage of endometrial and ovarian cancers (Toffoli et al., *Int J Cancer.* Apr. 22, 1997; 74(2):193-198). High levels of FBP have also been associated with the more aggressive serous variant of endometrial cancer (Dainty et al., *Gyn Onc.* 2007; 105(3):563-570). Furthermore, FBP may also be associated with failure to respond to platinum-based chemotherapy and reduced survival in ovarian cancer patients with residual disease after surgical treatment (Toffoli et al., *Int J Cancer.* Apr. 17, 1998; 79(2):121-126).

Highlighting the importance of this TAA, there have already been significant efforts toward developing novel FBP-targeted therapies, including a monoclonal antibody, farletuzumab, alone or in conjugates to deliver radionuclides, FRα-targeted T cells and stimulatory cytokines to malignant tissues. Additionally, immunotherapy methods for FRα-expressing cancers currently being investigated include the use of folate-localized molecules to enhance cancer immunogenicity, techniques to raise FRα-specific immunity via viral vector, as well as multiple vaccine strategies including modified whole tumor cells, as well as DNA, dendritic cell and multi-peptide peptide vaccines (reviewed for example by Clifton et al., Human Vaccines 7:183-190, 2011).

Previous studies have shown that FRα contains naturally processed immunogenic peptides that are recognized by tumor-associated lymphocytes, and that two specific FRα-derived immunogenic peptides, E39 (FRα 191-199) and E41 (FRα 245-253), are capable of enhancing tumor-associated lymphocyte (TAL) proliferation and anti-tumor function (Peoples et al., Ann Surg Oncol 1998; 5:743-50). The HLA-A2 restricted E39 peptide has also been shown to enhance tumor-associated lymphocyte proliferation and anti-tumor function in pre-clinical trials (Kim et al., *Anticancer Res.* July-August 1999; 19(4B):2907-2916; Peoples et al., Ann Surg Oncol 1998; 5:743-50; Peoples et al., Clin Cancer Res 1999; 5:4214-23).

However, despite some promising results with various regimens, durability of response remains limited. Given the propensity for recurrence in patients with aggressive forms of endometrial cancer, a treatment with better long-term efficacy is needed.

SUMMARY OF THE INVENTION

The present invention is based, at least in part, that a vaccine containing the E39 peptide is effective in preventing recurrence of aggressive forms of endometrial and ovarian cancers which express low levels of FRα.

Accordingly, in one aspect, a method of preventing or reducing the risk of recurrence of an aggressive endometrial or ovarian cancer in a human subject is provided. The method comprises administering to the subject a vaccine comprising at least about 1.0 mg of a peptide comprising the amino acid sequence of SEQ ID NO: 1), and human granulocyte macrophage stimulating factor (GM-CSF) as an adjuvant every three to four weeks until protective immunity is established.

In some embodiments, the cancer is a serous variant of endometrial cancer. In one embodiment, the cancer is ovarian carcinoma. In one embodiment, the endometrial cancer is serous uterine cancer. In particular embodiments, the endometrial or ovarian cancer is characterized as a Stage II or higher cancer. In related embodiments, the endometrial or ovarian cancer is characterized as having a low expression level of FRα, for example, an immunohistochemistry (IHC) rating of 0 or 1+.

In some embodiments, the human subject has been previously treated (e.g., received a primary treatment) with one or more cancer therapies. In some embodiments, the primary treatment includes surgery, chemotherapy or a combination thereof. In one embodiment, the subject has no evidence of disease (NED) after completion of the primary treatment. In one embodiment, the peptide vaccine is administered within about three months after the primary treatment is completed.

In some embodiments, the vaccine is administered by inoculation or injection. In one embodiment, the vaccine is administered by intradermal injection in one dose or in one or more split dosages. In some embodiments, the vaccine is administered as split dosages that are administered substantially concurrently. In related embodiments, the split dosages are administered at one site or at different sites. In other related embodiments, the split dosages are administered at least 5 cm apart.

In some embodiments, the vaccine is administered every three to four weeks for a period of six months. In some embodiments, each administration of the vaccine occurs at the same site or at different sites. In one embodiment, each administration of the vaccine occurs in the same lymph node draining area.

In some embodiments, the GM-CSF is present in the vaccine in an amount between about 0.01 to about 0.5 mg GM-CSF. In one embodiment, the vaccine contains about 0.250 mg of GM-CSF. In one embodiment, the peptide consists of the amino acid sequence of SEQ ID NO: 1. In another embodiment, vaccine comprises a 1.0 of a peptide consisting of the amino acid sequence of SEQ ID NO: 1, and about 0.250 GM-CSF.

In a related aspect, a method for inducing and maintaining an immune response to an aggressive endometrial cancer in a human subject is provided. The method comprises (a) administering to the subject a vaccine comprising at least about 1.0 mg of a peptide comprising the amino acid sequence of SEQ ID NO: 1), and human granulocyte macrophage stimulating factor (GM-CSF) as an adjuvant every three to four weeks until protective immunity is established, and (b) administering a booster composition comprising a peptide comprising an amino acid selected from the group consisting of SEQ ID NO: 1 and SEQ ID NO: 2, and an adjuvant about six months, about twelve months or about one year after completion of the primary immunization schedule.

In one embodiment, the booster composition contains a peptide consisting of the amino acid sequence of SEQ ID NO: 1 or SEQ ID NO: 2. In one embodiment, the booster composition comprises a peptide consisting of the amino acid sequence of SEQ ID NO: 1. In one embodiment, the booster composition comprises an peptide consisting of the amino acid sequence of SEQ ID NO: 2.

In some embodiments, the booster composition comprises about 0.5 to about 1.0 mg of the peptide. In some embodiments, the adjuvant in the booster composition is GM-CSF in an amount between about 0.01 mg to about 0.5 mg GM-CSF. In one embodiment, the booster composition comprises about 0.250 GM-CSF.

Also provided are kits that include the peptide vaccines used in the methods of the invention. In one embodiment, the kit contains the E39 peptide vaccine in unit dosage form of about 1.0 mg. Other features and advantages of the instant disclosure will be apparent from the following detailed description and examples, which should not be construed as limiting.

BRIEF DESCRIPTION OF THE FIGURES

FIG. 8 (A) depicts the overall curves for control patients with IHC 0, 1+ vs. 2-4+; (B) depicts the overall survival curves for E39 treated patients with IHC 0, 1+ vs. 2-4+.

DETAILED DESCRIPTION OF THE INVENTION

Definitions

Figure 1:
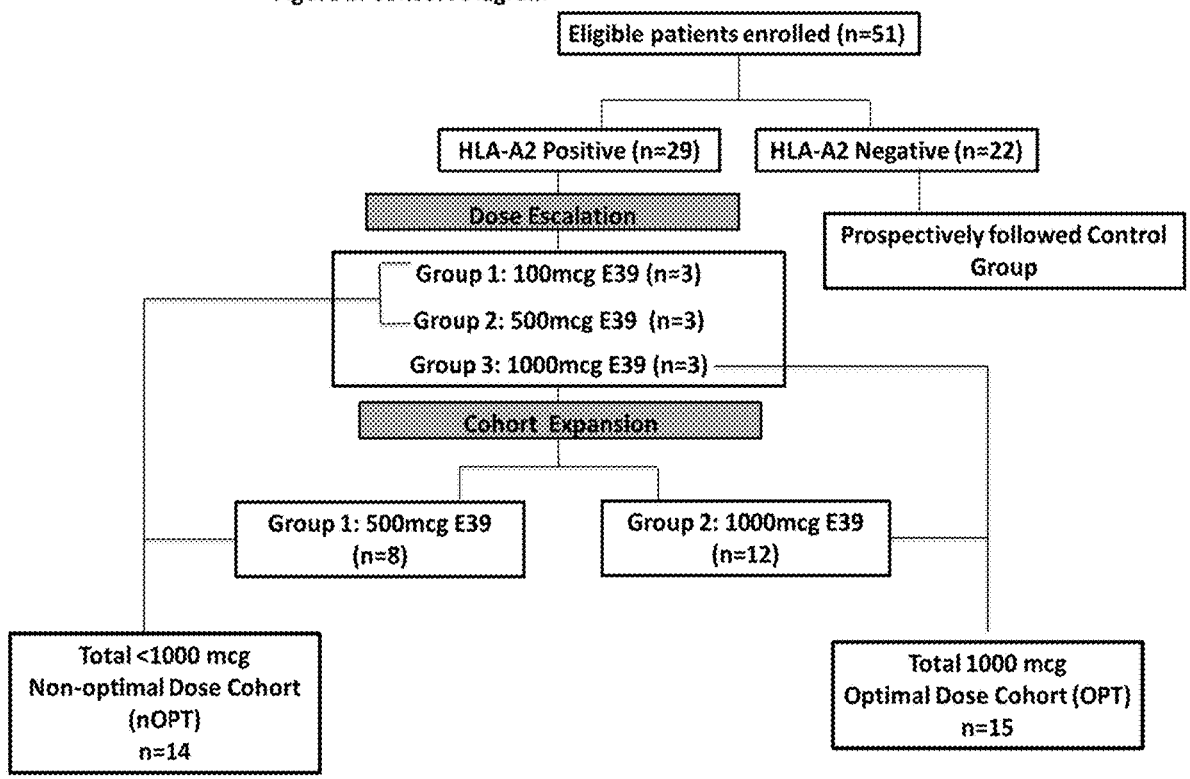
FIG. 1 is a flow diagram depicting the treatment protocol for patients enrolled in phaseI/IIa clinical trial.

In order that the present description may be more readily understood, certain terms are first defined. Additional definitions are set forth throughout the detailed description. Unless defined otherwise, all technical and scientific terms used herein have the same meaning as commonly understood by one of ordinary skill in the art, and conventional methods of immunology, protein chemistry, biochemistry, recombinant DNA techniques and pharmacology are employed.

As used herein, the singular forms "a", "an" and "the" include plural referents unless the context clearly dictates otherwise. The use of "or" or "and" means "and/or" unless stated otherwise. Furthermore, use of the term "including" as well as other forms, such as "include", "includes", and "included", is not limiting.

The term "about" as used herein when referring to a measurable value such as an amount, a temporal duration and the like, is encompasses variations of up to ±10% from the specified value. Unless otherwise indicated, all numbers expressing quantities of ingredients, properties such as molecular weight, reaction conditions, etc., used herein are to be understood as being modified by the term "about".

The term "antigen" as used herein is defined as an entity which elicits an immune system response. The term herein may be abbreviated to "Ag."

"Booster" refers to a dose of an immunogen administered to a patient to enhance, prolong, or maintain protective immunity and to overcome the down-regulation of T-cell responses mediated by regulatory T-cells.

The term "cancer" as used herein is defined as a tissue of uncontrolled growth or proliferation of cells, such as a tumor. As used herein, the term includes pre-malignant as well as malignant cancers. "Ovarian cancer" includes primary peritoneal or fallopian tube malignancies.

The term "endometrial cancer" as used herein refers generally to cancer arising from the lining (endometrium) of the uterus. An "aggressive endometrial cancer" can be a serous variant of endometrial cancer, or characterized based on histology as intermediate or high grade (grade 2 or 3), or stage II or higher.

The term "deplete" in the context the therapeutic methods disclosed herein refers to a reduction in the number of, or elimination of cancer cells expressing folate receptor alpha.

The terms "effective treatment" or "positive therapeutic response" are used interchangeably to refer to a course of treatment producing a beneficial effect, e.g., amelioration of at least one symptom of a disease or disorder. A beneficial effect can take the form of an improvement over baseline, i.e., an improvement over a measurement or observation made prior to initiation of therapy according to the methods provided herein, including slowing, stopping or reversing the progression of an endometrial cancer in a subject at any clinical stage, as evidenced by a decrease or elimination of a clinical or diagnostic symptom of the disease after administration of the FRα peptide vaccine in accordance with the methods described herein. Effective treatment may, for example, decrease in tumor size, decrease the presence of circulating tumor cells, reduce or prevent metastases of a tumor, slow or arrest tumor growth and/or prevent or delay tumor recurrence or relapse.

"Effective amount," or "therapeutically effective amount" are used interchangeably herein, and refer to an amount of a compound or composition, used according to the methods provided herein that is effective to inhibit the occurrence or ameliorate one or more clinical or diagnostic symptoms of a FRα expressing cancer, as determined by any means suitable in the art. Such results can include, but are not limited to, an increase in FRα-specific cytotoxic T-lymphocytes (CTLs), a decrease in circulating tumor cells, a decrease in tumor size, the cessation of tumor growth and/or the prevention or delay of tumor recurrence or relapse in a subject.

The term "epitope" as used herein is defined as a short peptide derived from a protein antigen which binds to an MHC molecule and is recognized by a particular T cell. An epitopic core sequence, as used herein, is a relatively short stretch of amino acids that is "complementary" to, and therefore will bind, receptors on CTLs. It will be understood that in the context of the present disclosure, the term "complementary" refers to amino acids or peptides that exhibit an attractive force towards each other.

As used herein, the term "an epitope(s) that is immunologically recognized by a CTL" is intended to refer to a peptide or protein antigen which includes a primary, secondary or tertiary structure similar to an epitope located within a FRα polypeptide. The level of similarity will generally be to such a degree that the same population of CTLs will also bind to, react with, or otherwise recognize, the cross-reactive peptide or protein antigen.

The term "folate receptor α" (also referred to as FRα, FRA, FR-alpha, FOLR-1, folate binding protein, FBP, FOLR1, LK26 trophoblastic antigen and GP38) refers to the alpha isoform of the high affinity receptor for folate. Membrane bound FRα is attached to the cell surface by a glycosyl phosphtidylinositol (GPI) anchor, recycles between extracellular and endocytic compartments and is capable of transporting folate into the cell. FRα is expressed in a variety of epithelial tissues including those of the female reproductive tract, placenta, breast, kidney, proximal tubules, choroid plexus, lung and salivary glands. Soluble forms of FRα may be produced by the action of proteases or phospholipase. As used herein "soluble FRα" refers to FRα that is not membrane bound and is present in biological fluids, e.g., serum or urine. For example, soluble FRα may be shed, secreted or exported from normal or cancerous cells into biological fluids.

(SEQ ID NO: 3)

```
tcaaggttaa acgacaagga cagacatggc tcagcggatg acaacacagc tgctgctcct   60
tctagtgtgg gtggctgtag tagggggaggc tcagacaagg attgcatggg ccaggactga  120
acttctcaat gtctgcatga acgccaagca ccacaaggaa aagccaggcc ccgaggacaa  180
gttgcatgag cagtgtcgac cctggaggaa gaatgcctgc tgttctacca acaccagcca  240
ggaagcccat aaggatgttt cctacctata tagattcaac tggaaccast gtggagagat  300
ggcacctgcc tgcaaacggc atttcatcca ggacacctgc ctctacgagt gctcccccaa  360
cttggggccc tggatccagc aggtggatca gagctggcgc aaagagcggg tactaaacgt  420 gccctgtgc aaagaggact gtgagcaatg gtgggaagat tgtcgcacct cctacacctg  480
```

```
                                -continued
caagagcaac tggcacaagg gctggaactg gacttcaggg tttaacaagt gcgcagtggg  540
agctgcctgc caacctttcc atttctactt ccccacaccc actgttctat acaatgaaat  600
ctggactcac tcctacaagg tcagcaacta cagccgaggg agtggccgct gcatccagat  660
gtggttcgac ccagcccagg gcaacccsaa tgagaagatg gcgaggttct atgctgcagc  720
catgagtggg gctgggccct gggcagcctg gcctttcctg cttagcctgg ccctaatgct  780
gctgtggctg ctcagctgac ctccttttac cttctgatac ctggaaatcc ctgccctgtt  840
cagccccaca gctcccaact atttggttcc tgctccatgg tcgggcctct gacagccact  900
ttgaataaac cagacaccgc acatgtgtct tgagaattat ttggaaaaaa aaaaaaaaaa  960
aa                                                                 962
                                                       (SEQ ID NO: 4)
Met Ala Gln Arg Met Thr Thr Gln Leu Leu Leu Leu Leu Val Trp Val

Ala Val Val Gly Glu Ala Gln Thr Arg Ile Ala Trp Ala Arg Thr Glu

Leu Leu Asn Val Cys Met Asn Ala Lys His His Lys Glu Lys Pro Gly

Pro Glu Asp Lys Leu His His Gln Cys Arg Pro Trp Arg Lys Asn Ala

Cys Cys Ser Thr Asn Thr Ser Gln Glu Ala His Lys Asp Val Ser Tyr

Leu Tyr Arg Phe Asn Trp Asn His Cys Gly Glu Met Ala Pro Ala Cys

Lys Arg His Phe Ile Gln Asp Thr Cys Leu Tyr Glu Cys Ser Pro Asn

Leu Gly Pro Trp Ile Gln Gln Val Asp Gln Ser Trp Arg Lys Glu Arg

Val Leu Asn Val Pro Leu Cys Lys Glu Asp Cys Glu Gln Trp Trp Glu

Asp Cys Arg Thr Ser Tyr Thr Cys Lys Ser Asn Trp His Lys Gly Trp

Asn Trp Thr Ser Gly Phe Asn Lys Cys Ala Val Gly Ala Ala Cys Gln

Pro Phe His Phe Tyr Phe Pro Thr Pro Thr Val Leu Cys Asn Glu Ile

Trp Thr His Ser Tyr Lys Val Her Asn Tyr Ser Arg Gly Ser Gly Arg

Cys Ile Gln Met Trp Phe Asp Pro Ala Gln Gly Asn Pro Asn Glu Glu

Val Ala Arg Phe Tyr Ala Ala Ala Met Ser Gly Ala Gly Pro Trp Ala

Ala Trp Pro Phe Leu Leu Ser Leu Ala Leu Met Leu Leu Trp Leu Leu

Ser
```

"Free of cancer" or "disease free" or NED (No Evidence of Disease) means that the patient is in clinical remission induced by treatment with the current standard of care therapies. By "remission" or "clinical remission," which are used synonymously, it is meant that the clinical signs, radiological signs, and symptoms of cancer have been significantly diminished or have disappeared entirely based on clinical diagnostics, although cancerous cells can still exist in the body. Thus, it is contemplated that remission encompasses partial and complete remission. The presence of residual cancer cells can be enumerated by assays such as CTC (Circulating Tumor Cells) and can be predictive of recurrence.

The term "immune response" as used herein refers to a cellular immune response, including eliciting stimulation of T lymphocytes, macrophages, and/or natural killer cells.

The term "immunity" as used herein is defined as the ability to provide resistance to a tumor resulting from exposure to an antigen that is a folate binding protein epitope.

The term "inhibit" or "inhibition" means to reduce by a measurable amount.

The "level" of a specified protein refers to the amount of protein in a sample as determined using any method known in the art for measuring protein levels, including electrophoresis, capillary electrophoresis, high performance liquid chromatography (HPLC), thin layer chromatography (TLC), hyperdiffusion chromatography, fluid or gel precipitation reactions, absorption spectroscopy, colorimetric assays, spectrophotmetric assays, flow cytometry, immmunodiffusion, solution phase assay, immunoelectrophoresis, Western blotting, radioimmunoassay (MA), enzyme-linked immunosorbent assays (ELISAs), immunofluorescent assays and electrochemiliminescence immunoassays.

"Peptide" refers to any peptide comprising two or more amino acids joined by peptide bonds or modified peptide bonds (e.g., peptide isosteres). Peptides can contain amino acids other than the 20 naturally occurring nucleic acid encoded amino acids, and include amino acid sequences modified either by natural processes, such as post-translational processing, or by chemical modification techniques which are well known in the art. Modifications can occur anywhere in a peptide, including the peptide backbone, the amino acid side-chains and the amino or carboxyl termini. It will be appreciated that the same type of modification can be present in the same or varying degrees at several sites in a given peptide. Also, a given polypeptide can contain many types of modifications. Polypeptides can be branched as a result of ubiquitination, and they can be cyclic, with or without branching. Cyclic, branched and branched cyclic polypeptides can result from natural posttranslational processes or can be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The term "prevent" refers to any success or indicia of success in the forestalling of cancer recurrence or relapse in a subject in clinical remission, as measured by any objective or subjective parameter, including the results of a radiological or physical examination, or in the level of circulating tumor cells.

"Protective immunity" or "protective immune response" means that a subject mounts an active immune response to an immunogenic component of an antigen such as the FRα antigens described and exemplified herein, such that upon subsequent exposure to the antigen, the subject's immune system is able to target and destroy cells expressing the antigen, thereby decreasing the incidence of morbidity and mortality associated with cancer in the subject. For example, protective immunity in the context of the present methods is conferred at least partially by T lymphocytes.

"Optimal biologic dose (OBD)" is defined as the minimum dose of a drug that gives the most optimal and lasting in vivo response without clinically unacceptable toxicity. For example, the OBD of a peptide vaccine is the amount that gives the most optimal and lasting in vivo immunologic response to the peptide.

"Relapse" or "recurrence" or "resurgence" are used interchangeably herein, and refer to the radiographic diagnosis of return, or signs and symptoms of return of cancer after a period of improvement or remission.

The term "sample" refers to a collection of fluids, cells or tissues isolated from a subject. Biological fluids are typically liquids at physiological temperatures and may include naturally occurring fluids present in, withdrawn from, expressed or otherwise extracted from a subject or biological source. Examples of biological fluids include blood, serum, serosal fluids, plasma, lymph, urine, cerebrospinal fluid, saliva, ocular fluids, cystic fluid, tear drops, feces, sputum, mucosal secretions, vaginal secretions, gynecological fluids, ascites fluids such as those associated with non-solid tumors, fluids of the pleural, pericardial, peritoneal, abdominal and other body cavities, fluids collected by bronchial lavage and the like.

The term "control sample", as used herein, refers to any clinically relevant control sample, including, for example, a sample from a healthy subject or a sample made at an earlier timepoint from the subject to be assessed. For example, the control sample can be a sample taken from the subject prior to onset of cancer, at an earlier stage of disease, or before the administration of treatment or of a portion of treatment.

The term "subject" or "patient" are used interchangeably herein and refer to a mammal such as a human, mouse, rat, hamster, guinea pig, rabbit, cat, dog, monkey, cow, horse, pig and the like.

As used herein, "substantially purified" refers to a vaccine component (e.g, a protein, polypeptide, or peptide) that has a level of purity where the compound is substantially free from other chemicals, biomolecules or cells. For example, a substantially purified vaccine component is about 60%, about 70%, about 80%, about 90%, about 95%, about 99% or more a free of the other components of the manufacturing process (e.g., cellular extract or reagents of chemical synthesis). Various techniques suitable for use in chemical, biomolecule or biological purification, well known to those of skill in the art, may be applicable to preparation of a vaccine component of the present invention. These include, for example, precipitation with ammonium sulfate, polyethylene glycol (PEG), antibodies and the like or by heat denaturation, followed by centrifugation; fractionation, chromatographic procedures, including but not limited to, partition chromatograph (e.g., paper chromatograph, thin-layer chromatograph (TLC), gas-liquid chromatography and gel chromatography) gas chromatography, high performance liquid chromatography, affinity chromatography, supercritical flow chromatography ion exchange, gel filtration, reverse phase, hydroxylapatite, lectin affinity; isoelectric focusing and gel electrophoresis (see for example, Sambrook et al. 1989; and Freifelder, Physical Biochemistry, Second Edition, pages 238-246, incorporated herein by reference).

The term "variant" as used herein is defined as a modified or altered form of a wildtype sequence. The term "folate binding protein variant" as used herein is defined as a folate binding protein and peptides thereof which are preferably recognized by helper T cells or cytotoxic T cells and may be naturally derived, synthetically produced, genetically engineered, or a functional equivalent thereof, e.g. where one or more amino acids may be replaced by other amino acid(s), (e.g., or non-amino acid(s) which do not substantially affect function. In some embodiments, the variant may contain an altered side chain for at least one amino acid residue.

Various aspects described herein are described in further detail in the following subsections.
Peptides The peptides used in the vaccine composition according to the methods of the invention comprise the FRα epitope E39 having the amino acid sequence EIWTHSYKV (SEQ ID NO: 1).

Peptides for use in the vaccine composition in accordance with the methods provided herein will generally be on the order of 9 to 20 amino acids in length, and more preferably about 9 to about 15 amino acids in length, and comprise the epitope core sequence of E39 (SEQ ID NO: 1). In certain embodiments, the peptides are at least about 9, 10, 11, 12, 13, 14, 15, 16, 17, 18, 19 or 20 amino acids in length. In one particular embodiment, the peptide in the vaccine composition consists of the amino acid sequence of E39.

The peptides used in the booster composition according to the methods of the invention comprise the E39 peptide amino acid sequence (SEQ ID NO: 1), or the amino acid sequence of a modified FRα epitope such as E39' having the amino acid sequence EIWTFSTKV (SEQ ID NO: 2). In one embodiment, the peptide in the booster compositions consists of the amino acid sequence of E39 (SEQ ID NO: 1), and E39' (SEQ ID NO: 2).

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

Pharmaceutical Compositions

The vaccine and booster peptide compositions can be formulated as freeze-dried or liquid preparations according to any means suitable in the art. Peptide compositions comprising the E39 or E39' peptide antigens can be prepared using techniques well known to those skilled in the art including, but not limited to, mixing, sonication and microfluidation.

The peptide compositions can be formulated in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In general, the peptide compositions typically comprise a pharmaceutically acceptable carrier. As used herein, the term "pharmaceutically acceptable" means approved by a government regulatory agency or listed in the U.S. Pharmacopeia or another generally recognized pharmacopeia for use in animals, particularly in humans. The term "carrier" refers to a diluent, adjuvant, excipient, or vehicle with which the compound is administered.

In certain embodiments, the peptide compositions are provided in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

In one embodiment, the peptide compositions are formulated for inoculation or injection, for example, either subcutaneously (intradermally) or intramuscularly into the subject.

Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, water-in-oil dextrose solution, propylene glycol solutions, water-in-oil emulsions, biodegradable oil vehicles, oil-in-water emulsions, liposome emulsions, and the like, and combinations thereof, preferably in sterile form.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of dimethyl sulfoxide (DMSO) as solvent is envisioned to result in extremely rapid penetration, delivering high concentrations of the active agents to a small area.

In one embodiment, the peptide compositions are provided in bacteriostatic water. In another embodiment, the peptide compositions are stored at or near 0° C. and thawed prior to use.

In alternative embodiments, the vaccine compositions can also be formulated in sustained release vehicles or depot preparations. Such long acting formulations can be administered by inoculation or implantation (for example subcutaneously or intramuscularly) or by injection. Thus, for example, the vaccine compositions can be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers.

In addition, if desired, the peptide compositions may contain minor amounts of auxiliary substances such as wetting or emulsifying agents, pH buffering agents, bacteriostatic agents and/or antioxidants. Suitable agents which prevent the action of microorganisms can be brought about by preservatives such as various antibacterial and antifungal agents, including but not limited to parabens (e.g, methylparabens, propylparabens), chlorobutanol, phenol, sorbic acid, thimerosal or combinations thereof. Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9±0.2%. Suitable antioxidants and stabilizers include sodium bisulfite, sodium metabisulfite, sodium thiosulfate, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethyl-propylcellulose, lanolin, methylcellulose, petrolatum, polyethylene glycol, polyvinyl alcohol, polyvinylpyrrolidone, carboxymethylcellulose and the like.

Biological Response Modifiers

In some embodiments, it may be desirable to coadminister biological response modifiers (BRMs), which have been shown to upregulate T cell immunity or down-regulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as γ-interferon, IL-2, or IL-12 or genes encoding proteins involved in immune helper functions, such as B-7.

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

In one embodiment, the methods of the invention further include administration of an immunostimulatory cocktail called COVAX, consisting of a Toll-like receptor 7 (TLR7) agonist (e.g., imiquimod cream), an agonistic anti-CD40 antibody, and interleukin-2 (IL-2).

Patient Selection

Provided herein are effective methods for treating patients having an endometrial or ovarian cancer. In certain embodiments, the endometrial cancer is a serous variant endometrial cancer. In another embodiment, the cancer is ovarian cancer. In another particular embodiment, the endometrial cancer is serous uterine carcinoma.

In some embodiments, the endometrial or ovarian cancer expresses a low level of FRα. Art recognized techniques for determining the FRα protein or nucleic acid expression levels. For example, the tumor can be biopsied and protein or nucleic acid expression level of FRα determined by immunohistochemistry or fluorescence in situ hybridization using as previously described (e.g., Shia et al. Human Pathol. 39:498-505, 2008; Leung et al. Clin. Biochem 46; 1462-1468, 2013; O'Shannessy et al. OncoTarget. 2:1227-1243, 2011).

In certain embodiments, the endometrial or ovarian cancer has an IHC rating of 0 or 1+ for FRα protein expression. The IHC rating of FRα is determined according to known techniques (e.g., Markert et al. Anticancer Res. 28:3567-3572, 2008).

In certain embodiments, the patient has been diagnosed with a primary cancer, i.e., the cancer is not a recurrence of previously diagnosed tumor after prior treatment.

In related embodiments, the patient has no evidence of disease following at least one chemotherapy-containing regimen that is considered standard of care for that cancer type.

In another embodiment, the patient meets one or more of the following clinical criteria:
(1) no evidence of disease (NED) after completion of primary first-line therapies (i.e., surgery, chemotherapy, immunotherapy and radiation therapy as appropriate per standard of care for patient's specific cancer);
(2) post-menopausal or rendered surgically infertile;
(3) good performance status (Karnofsky>60%, ECOG≤2), CBC, CMP and A-125.

Treatment Regimens

The primary immunization schedule for a subject is sufficient to induce and/or sustain a therapeutically effective immune response to FRα. For example, a therapeutically effective amount will provide a clinically significant increase in the number of E39-specific cytotoxic T-lymphocytes (CD8$^+$) in the subject, as well as a clinically significant increase in the cytotoxic T-lymphocyte response to the FRα antigen, as measured by any means suitable in the art. A therapeutically effective amount can also destroy residual microscopic disease and significantly reduce or eliminate the risk of cancer recurrence in the subject.

Suitable treatment protocols or regimens for inducing therapeutic immunity against an endometrial tumor characterized as having low FRα expression (IHC of 0 to 1+) include administering to the subject a peptide vaccine comprising about 1.0 mg of peptide consisting of the amino acid sequence of SEQ ID NO: 1 and an adjuvant (GM-CSF) every three to four weeks for a period of at least about six months.

In certain embodiments, the primary immunization schedule comprises a period of about six months in which a vaccine comprising 1 mg of the E39 peptide and 0.250 mg of GM-CSF is administered every three to four weeks as a split inoculation by concurrent injections about 5 cm apart on the patient's body, for a total of six doses during a six month period.

In certain embodiments, the primary immunization schedule is started after completion of prior treatment according to the accepted standard of care for the cancer type, including, but not limited to surgery, radiation, targeted therapy, chemotherapy, growth factor inhibitors, anti-angiogenesis factors or a combination of one or more thereof. In some embodiments, the subject will have received surgical resection of the endometrial tumor, first-line platinum-based therapy, first-line taxane-based therapy or a combination thereof prior to treatment with the E39 peptide vaccines. In some embodiments, a subject receives surgery, platinum, taxane, and avastin.

In particular embodiments, the primary immunization schedule is started about 4 months, 3 months, 2 months or less after the prior cancer treatment. In one embodiment, the primary immunization schedule is started no more than three months after completion of prior cancer treatment.

In other aspects, the methods further provide administration of a booster composition once the primary immunization schedule has been completed to bolster and/or sustain the therapeutic immunity to FRα. Booster compositions contain a peptide comprising the amino acid sequence of E39 (SEQ ID NO: 1) or E39' (SEQ ID NO: 2) and an adjuvant. The booster composition can be administered at regular intervals of about 3, about 6, about 9 or about 12 months after completion of the primary immunization schedule. In a particular embodiment, the booster composition is administered about every 6 months. In an alternative embodiment, boosters can be administered on an as-needed basis, for example, based on when there is a decrease in the FRα immune response (as measured, e.g, by CTL or antibody titers), or an increase in circulating FRα-expressing tumor cells in the subject.

Administration of the peptide vaccine and booster compositions can be by infusion or injection (e.g., intravenously, intramuscularly, intracutaneously, subcutaneously, intrathecally, intraduodenally, intraperitoneally, and the like). The peptide vaccine compositions can also be administered intranasaly, vaginally, rectally, orally or transdermally. In a particular embodiment, the peptide vaccine compositions are administered by intradermal injection.

In some embodiments, each dose of the peptide vaccine and booster compositions can be split into multiple injections, which are administered preferably substantially concurrently. When administered as a split inoculation, the dose of the peptide vaccine or booster composition is preferably, but not necessarily, proportioned equally in each separate injection. In addition, the dose of the adjuvant is preferably, but not necessarily, proportioned equally in each separate injection. The separate injections for the split inoculation are preferably administered substantially proximal to each other on the patient's body. In one embodiment, the injections are administered at least about 1 cm apart from each other on the body. In another embodiment, the injections are administered at least about 2.5 cm apart from each other on the body. In a particular embodiment, the injections are administered at least about 5 cm apart from each other on the body. In another embodiment, the injections are administered at least about 10 cm apart from each other on the body. In other embodiments, the injections are administered more than 10 cm apart from each other on the body, for example, at least about 12.5, 15, 17.5, 20 cm or more apart from each other on the body. Primary immunization injections and booster injections can be administered as a split inoculation as described and exemplified herein.

The booster compositions used in the methods provided herein comprise about 0.1 to about 2.0 mg of either the E39 or E39' peptide. In one embodiment, the booster composition comprises about 500 mcg, about 600 mcg, 700 mcg, 800 mcg, 900 mcg or 1000 mcg of the E39 peptide. In another embodiment, the booster composition comprises about 500 mcg, about 600 mcg, 700 mcg, 800 mcg, 900 mcg or 1000 mcg of the E39' peptide. In one preferred embodiment, the booster composition comprises about 500 mcg or about 1000 mcg of the E39 peptide. In a particular embodiment, the booster composition contains about 500 mcg or about 1000 mcg of the E39' peptide.

In some embodiments, the adjuvant in the vaccine and booster composition can comprise from about 10% to about 50% (v/v), preferably about 20% to about 40% (v/v), and more preferably about 20% to about 30% (v/v) of the vaccine and booster compositions. In certain embodiments, the adjuvant is granulocyte macrophage-colony stimulating factor (GM-CSF). In one preferred embodiment, the vaccine and/or booster compositions comprise from about 0.01 mg to about 0.5 mg of GM-CSF. In another preferred embodiment, the vaccine and/or booster compositions comprise about 0.125 mg of GM-CSF. In another preferred embodiment, the vaccine and/or booster compositions comprise about 0.250 mg of GM-CSF.

After a period of about 48 hours after each dose of the vaccine composition is administered, the injection site can be assessed for local reaction of erythema and induration. If the reactions at both sites are confluent and the area of total induration measures >100 mm (or the patient experiences any >grade 2 systemic toxicity), then the dose of GM-CSF can be reduced, for example, by half, though it is intended that the peptide dose remain the same. If the patient presents a robust reaction on subsequent doses, then further reduction of GM-CSF can occur, for example, reducing by half. If the patient does not present with a robust reaction, then the patient can continue with the higher GM-CSF dose.

In other embodiments, the administration schedule and dosing of the booster is similarly determined, with boosters beginning with administration of vaccine compositions comprising 1 mg of E39 or E39' and 0.25 mg GM-CSF, administered about every six months following the conclusion of the primary immunization vaccine schedule.

Therapeutic Response

Subjects treated according to the methods disclosed herein may experience improvement in at least one sign or symptom associated with endometrial cancer.

In one embodiment, the subject experiences tumor shrinking and/or decrease in growth rate, i.e., suppression of tumor growth. In another embodiment, recurrence of the tumor is prevented or delayed. In related embodiments, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; and progression free survival (PFS) is increased.

In some embodiments, therapeutic response is measured by a reduction in the quantity and/or size of measurable tumor lesions. Measurable lesions are defined as those that can be accurately measured in at least one dimension (longest diameter is to be recorded) as ≥10 mm by CT scan (CT scan slice thickness no greater than 5 mm), 10 mm caliper measurement by clinical exam or >20 mm by chest X-ray. The size of non-target lesions, e.g., pathological lymph nodes can also be measured for improvement. In one embodiment, lesions can be measured on chest x-rays or CT or MRI films.

In other embodiments, cytology or histology can be used to evaluate responsiveness to a therapy. The cytological confirmation of the neoplastic origin of any effusion that appears or worsens during treatment when the measurable tumor has met criteria for response or stable disease can be considered to differentiate between response or stable disease (an effusion may be a side effect of the treatment) and progressive disease.

In yet another embodiment, therapeutic response is measured by a decrease in recurrence rate of the endometrial tumor in the subject when compared to the average recurrence rate in untreated control subjects. Recurrence of lack thereof can be expressed as disease-free survival (DFS) or recurrence-free survival (RFS) using clinically acceptable criteria.

In other embodiments, the subject experiences one or more of the following: a clinically significant increase in FRα-CTL activity; a clinically significant decrease in serum FRα levels; a clinically significant decrease serum CA125 levels; and a clinically significant decrease in circulating tumor cells (CTC) expressing FRα.

Exemplary therapeutic responses to therapy may include:
Disease Free Survival (DFS): At least a 10% delay in the time to recurrence of detectable disease;
Partial Response (PR): At least a 30% decrease in the sum of dimensions of target lesions, taking as reference the baseline sum diameters;
Stable Disease (SD): Neither sufficient shrinkage to qualify for partial response, nor sufficient increase to qualify for progressive disease, taking as reference the smallest sum diameters while on study; or
Complete Response (CR): Disappearance of all non-target lesions and normalization of tumor marker level. All lymph nodes must be non-pathological in size (<10 mm short axis).
Non-CR/Non-PD refers to a response presenting a persistence of one or more non-target lesion(s) and/or maintenance of tumor marker level above the normal limits.

Progressive Disease (PD) refers to a response presenting at least a 20% increase in the sum of dimensions of target lesions, taking as reference the smallest sum on study (this includes the baseline sum if that is the smallest on study). In addition to the relative increase of 20%, the sum must also demonstrate an absolute increase of 5 mm. The appearance of one or more new lesions is also considered progression.

In some embodiments, an effective amount of the compositions provided herein produce at least one therapeutic effect selected from the group consisting of reduction in size of a FRα-expressing tumor, reduction in metastasis, complete remission, partial remission, stable disease, increase in overall response rate, a pathologic complete response or a delay in tumor recurrence. In other embodiments, the improvement of clinical benefit rate is about 10%-20%, 30%, 40%, 50%, 60%, 70%, 80% or more.

Combination Treatments

The present methods can be combined with other means of cancer treatment including, but not limited to surgery, radiation, targeted therapy, chemotherapy, growth factor inhibitors, anti-angiogenesis factors or a combination of one or more thereof.

In particular embodiments, the patient receives treatment with one or more cancer therapies at least 12 hours, one day, a week, a month, six weeks, two months or three months prior to administration of the E39 peptide vaccine composition. In another embodiment, during the course of administration of the E39 and/or E39' peptide vaccines, a patient is treated concurrently with one or more additional cancer therapies.

In other embodiments, the patient may receive one or more additional cancer therapies subsequent to administration of the E39 peptide vaccine composition. For example, vaccination against FRα-specific antigens may sensitize the endometrial tumor against subsequent chemotherapeutic treatment. Without being bound by any one theory, it is possible that chemotherapy-induced systemic effects (e.g., enhanced cross-presentation of tumor antigens, depletion of suppressor cells, activation of DCs) may further promote the antitumor activity of FRα-specific CTLs.

In other embodiments, the additional cancer therapy is an anti-angiogenisis targeted therapy such as Bevacizumab (Avastin®), Aflibercept (VEGF Trap), Cediranib (Recentin™), Nintedanib (BIBF 1120), Pazopanib, Sorafenib (Nexavar®), Sunitinib (Sutent®), and Cabozantinib (XL-184); Ribose Polymerase (PARP) inhibitors, such as Olaparib (AZD2281), Iniparib (BSI-201), MK04827, ABT-888 and BMN-673; Phosphatidylinositol-3-kinase (PI3K)/Protein Kinase B (AKT)/mTOR pathway inhibitors, such as XL147, PX-866, Everolimus (Afinitor®), Temsirolimus (Torisel®) and Perifosine, MK-2206; SRC inhibitors such as Dasatinib (Sprycel®), and Saracatinib (AZD0530); EGFR Inhibitors such as cetuximab (Erbitux®), trastuzumab (Herceptin®), pertuzumab, erlotinib (Tarceva®), MM-121, and vandetanib; EGFRα inhibitors such as Farletuzumab (MORAb-003), EC145 (conjugate of folic acid and desacetylvinblastine); IGF inhibitors such as AMG 479 and dalotuzumab; p53 inhibitors such as MK-1775; and cytotoxic agents such as cyclophosphamide, carboplatin, pegylated liposomal doxorubisin (PLD), gemcitabine, paclitaxel, topotecan.

In some embodiments, the methods further include administration of a therapeutically effective amount of a platinum-containing compound and/or a taxane to the subject. Exemplary platinum-containing compounds include, but are not limited to, cisplatin and carboplatin. The platinum-containing compound may be administered to the subject about once every week, about once every two weeks, about once every three weeks, or about once every four weeks.

Examples of taxanes include, but are not limited to, paclitaxel, docetaxel, and semi-synthetic, synthetic, and/or modified versions and formulations thereof, including but not limited to nab-paclitaxel (Abraxane®), cabazitaxel (Jevtana®), DJ-927 (Tesetaxel®), paclitaxel poliglumex (Opaxoi®), XRP9881 (Larotaxel®), EndoTAG+pacitaxel (EndoTAG®-1), polymeric-micellar paclitaxel (Genexol-PM®), DHA-paclitaxel (Taxoprexin®), BMS-184476. The taxane may be administered to the subject once every week, about once every two weeks, about once every three weeks, or about once every four weeks. In embodiments in which both a platinum-containing compound and a taxane are administered to the subject prior to or as part of the treatment regimen, the platinum-containing compound may be administered before, after or simultaneously with the taxane.

Kits and Articles of Manufacture

Further provided are kits containing the peptide vaccine compositions described herein and instructions for use. Kits typically include a packaged combination of reagents in predetermined amounts with instructions and a label indicating the intended use of the contents of the kit. The term label or instruction includes any writing, or recorded material supplied on or with the kit, or which otherwise accompanies the kit at any time during its manufacture, transport, sale or use. It can be in the form prescribed by a governmental agency regulating the manufacture, use or sale of pharmaceuticals or biological products, which notice reflects approval by the agency of the manufacture, use or sale for administration to a human or for veterinary use. The label or instruction can also encompass advertising leaflets and brochures, packaging materials, and audio or video instructions.

For example, in some embodiments, the kit contains the peptide vaccine in a suitable container and instructions for administration. In some embodiments, the peptide vaccine is provided in a suitable container as a dosage unit for administration. Suitable containers include, for example, bottles, vials, syringes, and test tubes. The containers may be formed from a variety of materials such as glass or plastic.

In other embodiments, the peptide vaccine is provided in lyophilized form, and the kit may optionally contain a sterile and physiologically acceptable reconstitution medium such as water, saline, buffered saline, and the like. It may further include other materials desirable from a commercial and user standpoint, including other buffers, diluents, filters, needles, syringes, and package inserts with instructions for use, for example, comprising administration schedules, to allow a practitioner (e.g., a physician, nurse, or patient) to administer the composition contained therein.

INCORPORATION BY REFERENCE

All documents and references, including patent documents and websites, described herein are individually incorporated by reference to into this document to the same extent as if there were written in this document in full or in part.

The following examples are merely illustrative and should not be construed as limiting the scope of this disclosure in any way as many variations and equivalents will become apparent to those skilled in the art upon reading the present disclosure.

Example 1

Response to E39 in Patients with Endometrial or Ovarian Cancer

The purpose of this study was to test whether a peptide-based vaccine consisting of the E39 peptide mixed with the FDA-approved immunoadjuvant granulocyte macrophage colony-stimulating factor (GM-CSF) is safe and effective at inducing an in vivo peptide-specific immune response.

Methods

Patient Characteristics and Clinical Protocols

Eligible patients were identified with endometrial, ovarian, fallopian tube or peritoneal cancer and were disease-free after standard of care therapies. Patients were surgically or naturally post-menopausal. Exclusion criteria included patients currently receiving immunosuppressive therapy to include chemotherapy, steroids or methotrexate, poor health (ECOG<2), evidence of end-organ dysfunction, pregnancy, breast feeding, history of autoimmune disease, and involvement in other experimental protocols (except with permission of the principal investigator of the other study). Exclusion criteria included patients currently receiving immunosuppressive therapy to include chemotherapy, steroids or methotrexate, poor health (ECOG<2), evidence of end-organ dysfunction, pregnancy, breast feeding, history of autoimmune disease, and involvement in other experimental protocols.

Once enrolled, HLA status was evaluated to permit group assignment. E39 is a HLA-A2-restricted peptide (HLA-A2 is present in approximately 40-50% of the general population). HLA-A2 positive patients were thus inoculated with E39+GM-CSF, while HLA-A2 negative patients and those HLA-A2 positive individuals who declined vaccination were followed prospectively as matched controls for disease recurrence and progression. The clinical endpoints were long-term FBP immunity, time to recurrence from date of enrollment, and 2-year disease-free survival (DFS) rate. This planned interim analysis was performed 12 months after completion of trial enrollment.

Fifty-one (51) patients were enrolled in the study with twenty-nine HLA-A2+ patients in the vaccination group (VG), and twenty-two HLA-A2− patients as a control group (CG). The There were no significant differences in age, grade, stage, or histology between groups (all p>0.1). Demographic, safety, immunologic, and clinical recurrence (CR) data were collected. Disease free survival (DFS) was compared by Kaplan-Meir and logrank tests. Continuous variables were compared with analysis of variance and proportions with Fisher's exact test.

Vaccine and Vaccination Series

The E39 peptide (FBP 191-199, EIWTHSYKV) was produced commercially by an FDA-compliant production facility for patient use. The peptide was purified to >95% before use. Sterility, endotoxin (limulus amebocyte lysate test), and general safety testing was performed. In addition, the manufacturer performed purity/stability testing periodically. Single dose vials were tested for bacterial and fungal contaminants prior to use. The single dose vials were stored in the pharmacy at each institution. The bulk peptide was reconstituted to the following preparations: 100 mcg/0.5 mL, 500 mcg/0.5 mL, and 1000 mcg/0.5 mL. Each of these was mixed with 250 mcg/1.0 mL GM-CSF. This dose (250 mcg) of GM-CSF has been previously determined to be a safe and effective dose, based on our prior work with NeuVax[6].

The combination of peptide and adjuvant had a volume of 1.5 mL, which was administered intradermally in 0.75 mL inoculums at two different sites within 5 cm of each other. The primary vaccination series (PVS) consisted of six total vaccinations, one given every 21-28 days, administered in the same lymph node draining area.

Dosing

The phase I portion of this trial consisted of dose escalation to determine a safe and effective dose of the E39 peptide. The dose escalation scheme consisted of dosing cohorts of three patients receiving one the following doses: 100, 500, and 1,000 mcg of peptide, in addition to 250 mcg of GM-CSF. Prior to the fourth inoculation, each patient was assessed for liver, renal, and hematopoietic dysfunction. If organ function was stable and no dose limiting toxicity was observed, then the patient continued the series. After the third patient in a given dose group completed the third inoculation and organ function remained stable, the next dose group was initiated.

The optimal dose was initially defined immunologically, but was redefined when the 1000 mcg dosing cohort showed clinical benefit in initial survival data. This cohort was then expanded and became known as the optimal dose group (OPT). The phase IIa portion of this trial then analyzed the expanded OPT versus all other patients.

Toxicity

Standard local and systemic toxicities were collected and graded per the National Cancer Institute Common Terminology Criteria for Adverse Events, v4.03 toxicity scale. For the vaccine series (one vaccine/month for six months), patients were monitored closely for one hour after vaccine inoculation with questioning, serial exams and vital signs every 15 minutes to observe for a hypersensitivity reaction. Systemic toxicity and inoculation site local reactions were also determined after 48-72 hours.

In Vivo Immune Monitoring

Patients were assessed for evidence of in vivo immunologic response by evaluation of delayed-type hypersensitivity (DTH) reaction, which was measured pre-vaccination and again post-PVS. A DTH response was assessed with 100 mcg of E39 (without GM-CSF) as well as a parallel control (equivalent volume of sterile saline) injected intradermally at a site on the back or anterior thigh on the opposite side from the vaccination site. The response was measured using the sensitive ballpoint-pen method in 2 dimensions at 48-72 hours post injection[15]. The orthogonal mean was determined for each DTH; its correlation to immunologic response has been previously validated and used in our previous work[16]. These values were compared between pre-PVS and post-PVS.

Clinical Recurrences of Disease

Both the vaccinated patients and the observational control patients were monitored for evidence of clinical recurrence through the standard of care follow-up with their primary medical and/or surgical oncologist. This consisted of evaluations every three-months for the initial two years, then every six-months for an additional three years with clinical exam, laboratory tests and radiographic surveillance as indicated. Patients' clinical records were assessed for evidence of clinical recurrence. Disease free survival was measured from the date of enrollment. All patients were followed for clinical recurrence for up to two years at standard of care visits.

Statistical Analysis

A pre-specified, intention-to-treat analysis was performed at 12 months after the last patient was enrolled. Clinicopathologic data were compared between groups. Median and range were used to summarize continuous data and the groups were compared using a Mann-Whitney U test. Chi squared or Fischer exact test were used to compare categorical variables between groups. DTH data was presented as orthogonal means±standard errors and compared using a Student's t test. Time to recurrence was measured from the date of enrollment. DFS was analyzed using the Kaplan- Meier method, and groups were compared using a simple log-rank test. Statistical analyses were performed using SPSS version 22 (IBM Corp. Released 2013. IBM SPSS Statistics for Windows, Version 22.0. Armonk, N.Y.: IBM Corp.). Statistical significance was considered achieved if $p<0.05$. Pre-specified subset analyses were also performed by dose cohort.

Results

Patients

Fifty-one (51) patients were enrolled in the study, 29 in the vaccinated group (VG) and 22 patients in the control group (CG). Within the VG, 15 patients received the optimal dose (1000 mcg) of the peptide, referred to as the OPT group, while 14 patients received less, referred to as the non-optimal dose (nOPT) group (FIG. 1). There were no significant clinicopathologic differences between groups (Table 1A and 1B).

TABLE 1A

| Demographics | | | |
|---|---|---|---|
| Characteristic | Vaccinated (n = 29) | Controls (n = 22) | p-Value |
| Median age (yrs) | 60 | 61 | 0.790 |
| (Interquartile Range 1-3) | 52-67 | 53-63 | |
| Histology - n (%) | | | 0.373 |
| Endometrial | 6 (20.7) | 3 (13.6) | |
| Fallopian | 1 (3.4) | 0 (0.0) | |
| Ovarian | 20 (69.0) | 18 (86.4) | |
| Peritoneal | 2 (6.9) | 0 (0.0) | |
| Grade - n (%) | | | 0.851 |
| 1 (Well Differentiated) | 2 (6.9) | 2 (9.1) | |
| 2 (Moderately Differentiated) | 4 (13.8) | 2 (9.1) | |
| 3 (Poorly Differentiated) | 23 (79.3) | 18 (81.8) | |
| Stage - n (%) | | | 0.235 |
| Tis | 1 (3.4) | 0 (0.0) | |
| 1 | 6 (20.7) | 3 (13.6) | |
| 2 | 2 (6.9) | 4 (18.2) | |
| 3 | 14 (48.3) | 12 (54.5) | |
| 4 | 5 (17.2) | 3 (13.6) | |
| Tx | 1 (3.4) | 0 (0.0) | |
| Node - n (%) | | | 0.764 |
| Positive | 9 (31.0) | 5 (22.7) | |
| Negative | 20 (69.0) | 17 (77.3) | |
| FIGO Stage - n (%) | | | 0.591 |
| I | 4 (13.8) | 3 (13.6) | |
| II | 2 (6.9) | 3 (13.6) | |
| III | 18 (62.1) | 11 (50.0) | |
| IV | 5 (17.2) | 5 (22.7) | |

TABLE 1B

| Demographics - Dosing Cohorts | | | | |
|---|---|---|---|---|
| Characteristic | <1000 mcg (nOPT) (n = 14) | 1000 mcg (OPT) (n = 15) | Controls (n = 22) | p-Value |
| Median age (yrs) | 61 | 57 | 61 | 0.827 |
| (Interquartile range 1-3) | 56-66 | 49-67 | 53-63 | |
| Histology - n (%) | | | | 0.531 |
| Endometrial | 3 (21.4) | 3 (20.0) | 3 (13.6) | |
| Fallopian | 1 (7.1) | 0 (0.0) | 0 (0.0) | |
| Ovarian | 9 (64.3) | 11 (73.3) | 18 (86.4) | |
| Peritoneal | 1 (7.1) | 1 (6.7) | 0 (0.0) | |
| Grade - n (%) | | | | 0.508 |
| 1 (Well Differentiated) | 0 (0.0) | 2 (13.3) | 2 (9.1) | |
| 2 (Moderately Differentiated) | 3 (21.4) | 1 (6.7) | 2 (9.1) | |
| 3 (Poorly Differentiated) | 11 (78.6) | 12 (80.0) | 18 (81.8) | |
| T Stage - n (%) | | | | 0.263 |
| Tis | 0 (0.0) | 1 (6.7) | 0 (0.0) | |
| 1 | 3 (21.4) | 3 (20.0) | 3 (13.6) | |
| 2 | 0 (0.0) | 2 (13.3) | 4 (18.2) | |
| 3 | 9 (64.3) | 5 (33.3) | 12 (54.5) | |
| 4 | 2 (14.3) | 3 (20.0) | 3 (13.6) | |
| Tx | 0 (0.0) | 1 (6.7) | 0 (0.0) | |
| Node- n (%) | | | | 0.450 |
| Positive | 6 (42.9) | 3 (20.0) | 5 (22.7) | |
| Negative | 8 (57.1) | 12 (80.0) | 17 (77.3) | |
| FIGO Stage - n (%) | | | | 0.297 |
| I | 1 (7.1) | 3 (20.0) | 3 (13.6) | |
| II | 0 (0.0) | 2 (13.3) | 3 (13.6) | |
| III | 11 (78.6) | 7 (46.7) | 11 (50.0) | |
| IV | 2 (14.3) | 3 (20.0) | 5 (22.7) | |

Toxicity

Figure 2:
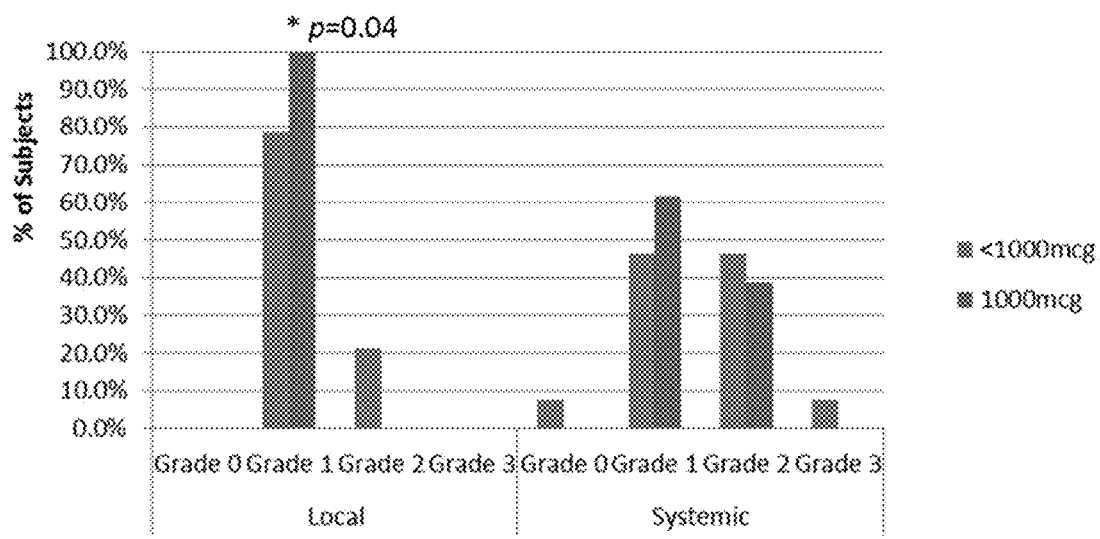
FIG. 2 is a bar graph depicting the maximum local systemic toxicity experienced by patients vaccinated with E39. There was a statistically significant different between the local toxicity experienced by the OPT vs nOPT group, p=0.04. No significant difference was noted within systemic toxicity.

Local and systemic toxicities were mild at the completion of the PVS (FIG. 2), with no grade 4 or 5 toxicities, and only 1 patient experiencing grade 3 toxicity. The maximum local toxicities were milder for the OPT patients than nOPT patients (p=0.04) with OPT and nOPT groups experiencing grade 1 (100% vs 78.6%) or grade 2 (0% vs 21.4%). The most common local toxicities were induration at the injection site, erythema, and pruritus. The maximum systemic toxicities for the OPT group as compared to the nOPT group were grade 0 (0% vs 7.7%), grade 1 (61.5% vs 46.2%), grade 2 (38.5% vs 46.2%) and grade 3 (0% vs 7.7%), (p>0.05 for each). The most common systemic toxicities were myalgias, headache, and fatigue (FIG. 1).

Immunologic Response

Figure 3:
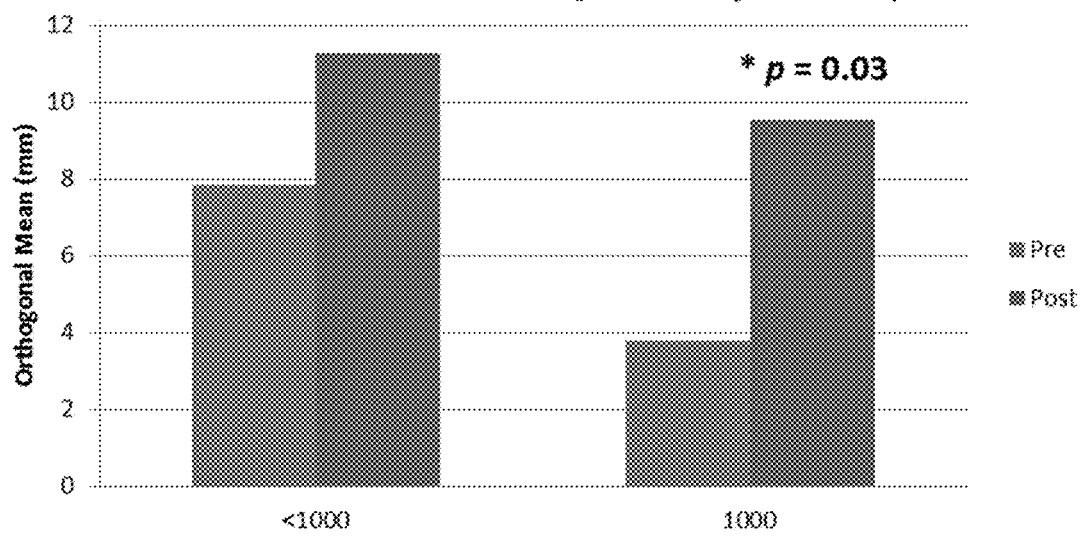
FIG. 3 is a bar graph depicting the local reactions to vaccination and DTH response before and after the primary vaccination series according to dosing cohorts expressed as the orthogonal mean of the reaction size and expressed as means. The average size of induration to E39 prior to vaccination was 5.7±1.5 mm compared to 10.3±2.8 mm post-vaccination (p=0.06). OPT patients had a statistically significant increase in pre-vaccination versus post-vaccination DTH (3.8±2.0 mm vs 9.5±3.5 mm, p=0.03), while nOPT patients experienced a smaller increase in pre-vs post-vaccination, which was not statistically significant (7.8±2.1 mm vs 11.3±4.8 mm, p=0.28).

The DTH increased from pre-vaccination to post-vaccination in the VG, approaching statistical significance (5.7±1.5 mm vs 10.3±2.8 mm, p=0.06). As shown in FIG. 3, when analyzed by dose, OPT patients had a statistically significant increase in DTH from pre-vaccination to post-vaccination (3.8±2.0 mm vs 9.5±3.5 mm, p=0.03), while nOPT patients experienced a smaller increase from pre- to post-vaccination, which was not statistically significant (7.8±2.1 mm vs 11.3±4.8 mm, p=0.28).

Disease-Free Survival

Figure 4:
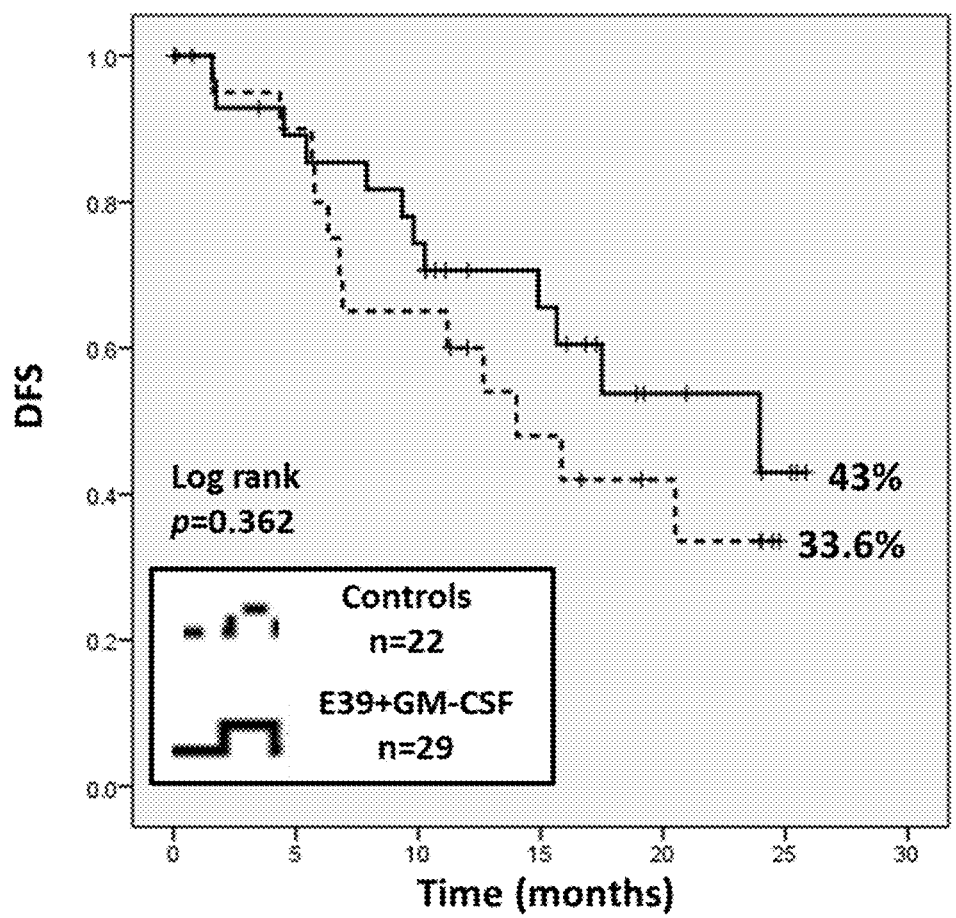
FIG. 4 depicts the 2-year estimated Kaplan Meier disease-free survival curves for vaccinated patients was 43% (95% confidence interval (CI): 18-66%) versus 33.6% (95% CI: 13-56%) in control patients (p=0.36). The vaccinated patients experienced a 31% reduction in relative recurrence risk regardless of dose.

An interim analysis was performed 12 months after completion of trial enrollment. The median follow up was 12.0 months (interquartile range 7.6-19.2 months). The overall recurrence rate for the VG versus the CG was 41.4% versus 54.6%, respectively (p=0.35). The 2-year estimated DFS for VG was 43% (95% confidence interval (CI): 18-66%) versus 33.6% (95% CI: 13-56%) in CG (p=0.36). The vaccinated patients experienced a 31% reduction in relative recurrence risk regardless of dose (FIG. 4).

Figure 5:
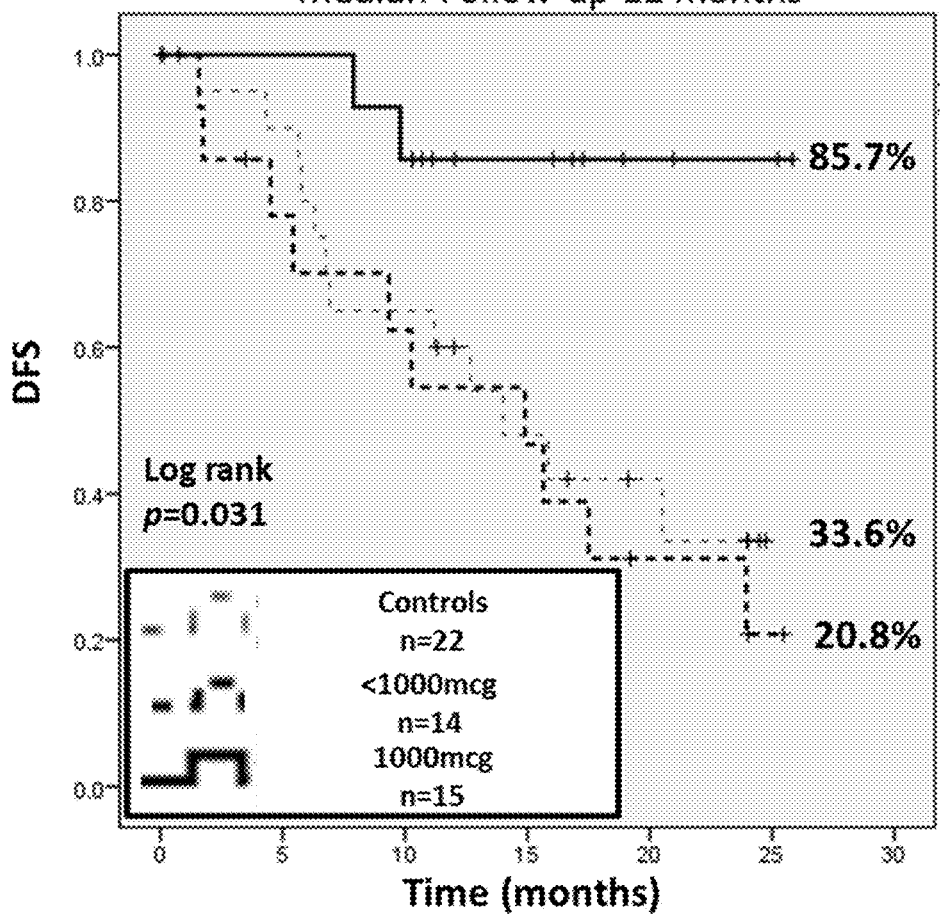
FIG. 5 depicts the 2-year estimated Kaplan Meier disease-free survival curves for the subgroup analysis performed based on E39 peptide dosing. The 2-year estimated DFS indicated a significant survival advantage for the OPT group at 85.7% (95% CI: 54-96%) compared to controls at 33.6% (95% CI: 13-56%) and the nOPT group at 20.8% (95% CI: 4-47%). Comparing the OPT and control groups, there was an 83% reduction in relative risk of recurrence.
Figure 6:
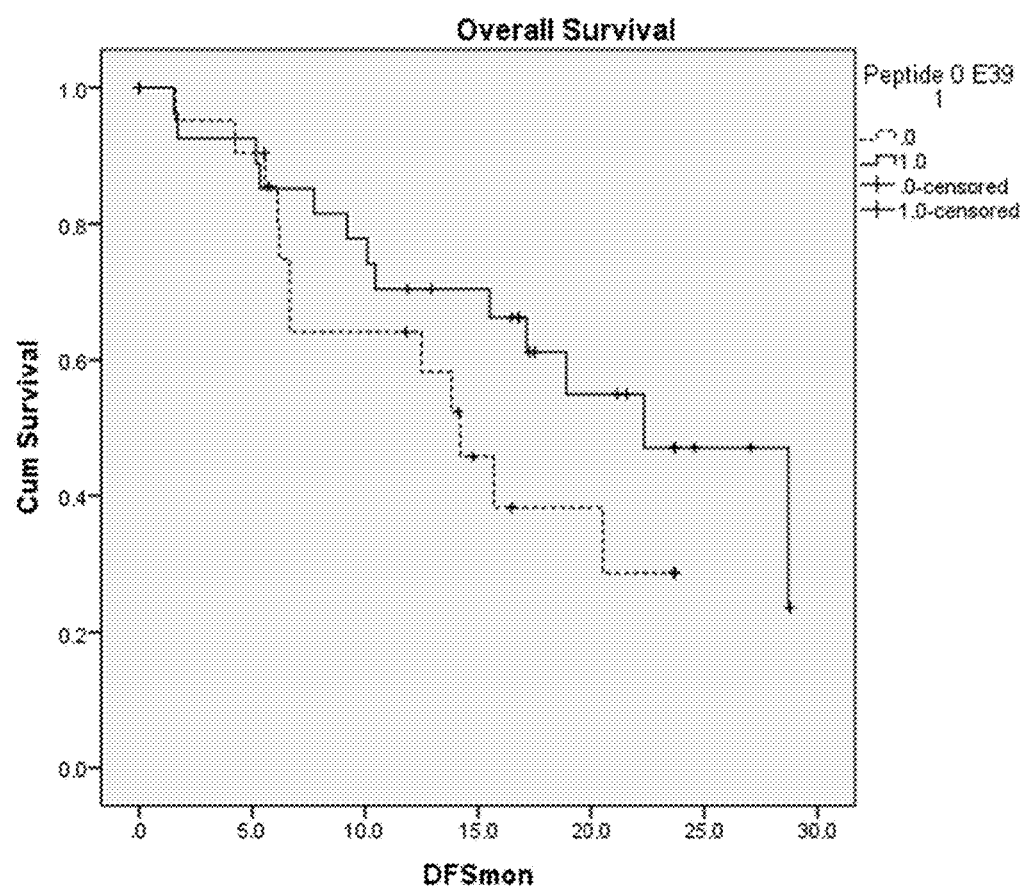
FIG. 6 depicts the overall disease-free survival curves for control and E39 treated patients.
Figure 7:
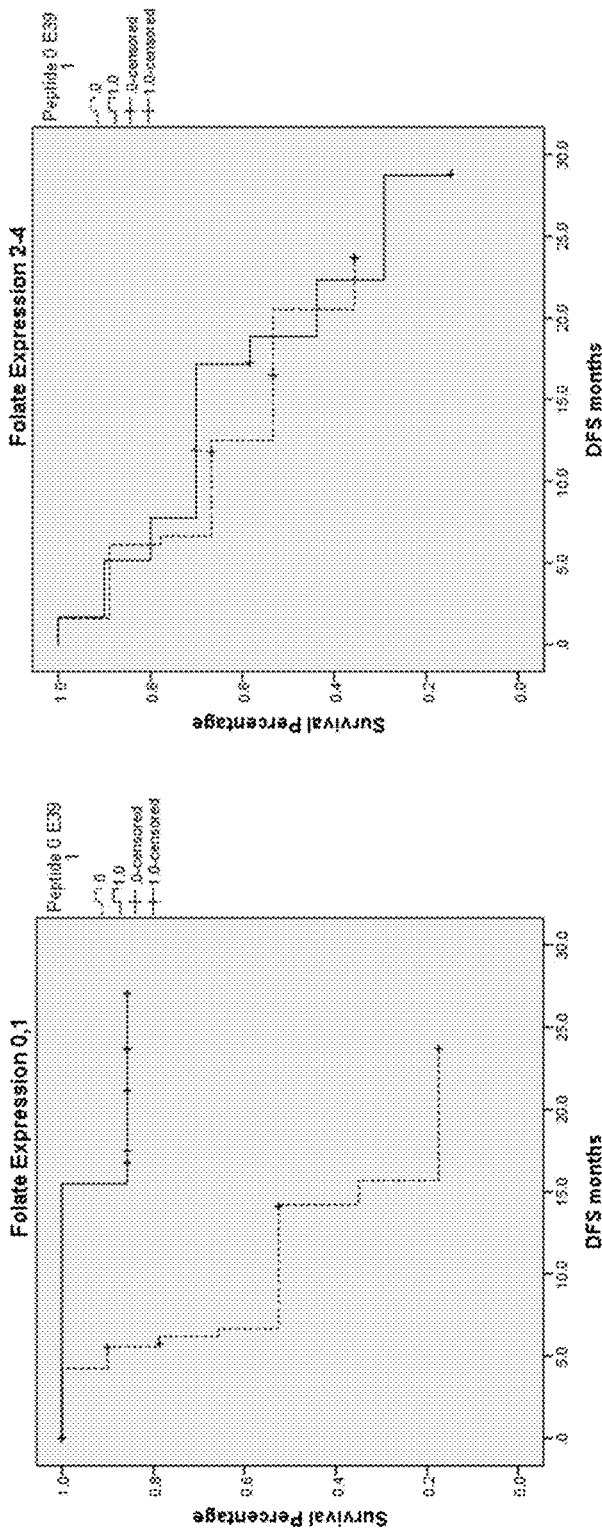
FIG. 7 (A) depicts the overall survival curves for control and E39 treated patients with IHC for FBP protein expression of 0 to 1+; (B) depicts the overall survival curves for control and E39 patients with IHC for FBP protein expression of 2-4+.
Figure 9:
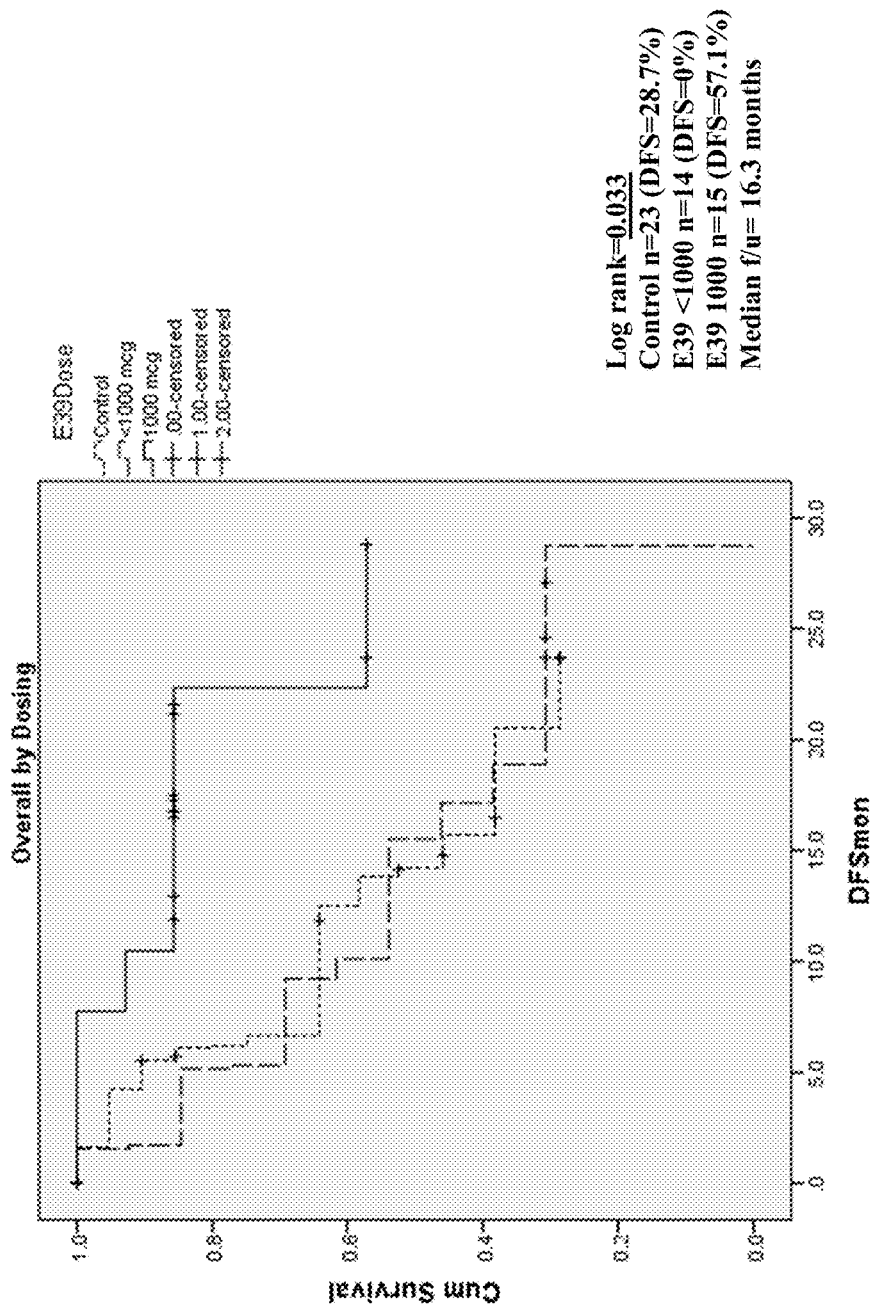
FIG. 9 depicts the overall survival curves for untreated control patients, patients treated with less than 1000 mcg E39, and patients treated with 1000 mcg E39.
Figure 10:
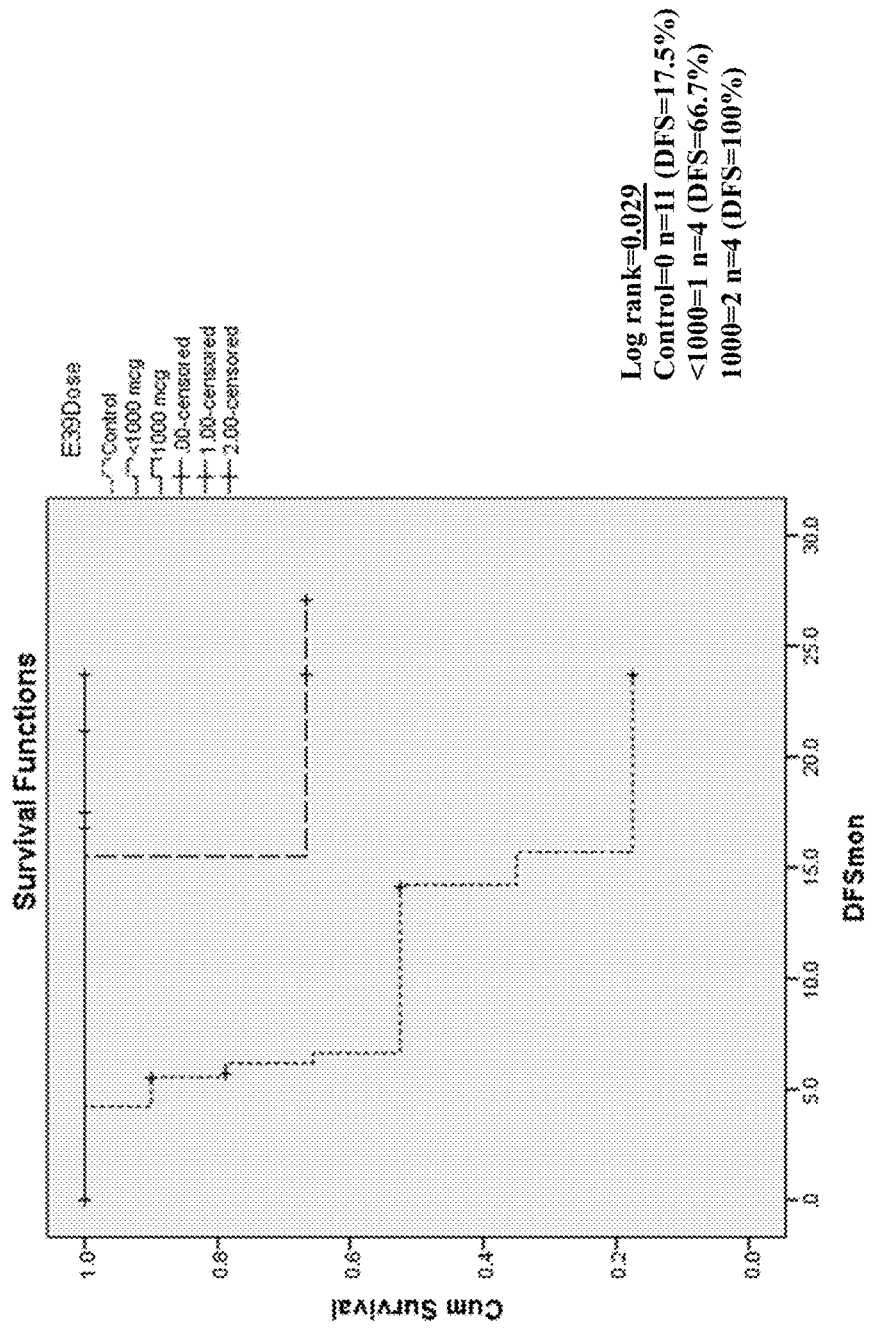
FIG. 10 depicts the overall survival curves for patients with FBP IHC 0 or 1+ treated with less than less than 1000 mcg E39, or patients treated with 1000 mcg E39.

Subgroup analyses were performed based on dosing cohort. The recurrence rate was significantly lower in the OPT group compared to the CG patients (13.3% vs 54.6%, p=0.02). There was no statistically significant difference in recurrence between the nOPT group versus the CG patients. When comparing the dosing cohorts, patients receiving the optimal dose of E39 experienced an 83% reduction in relative risk of recurrence compared to nOPT patients (HR 0.17, 95% CI: 0.04-0.77, p=0.003). The 2-year estimated DFS indicated a significant survival advantage for the OPT group at 85.7% (95% CI: 54-96%) compared to the controls at 33.6% (95% CI: 13-56%, p=0.02). Surprisingly, there was no difference of statistical significance in the estimated 2-year DFS between the nOPT and CG. A survival benefit was appreciated with analysis of the estimated 2-year DFS comparing OPT versus the nOPT patients, 85.7% versus 20.8% (p=0.009). FIG. 5 displays the survival analysis of a 3-way comparison between OPT, nOPT and CG.

Discussion

This trial using E39+GM-CSF to prevent recurrence in disease-free endometrial and ovarian cancer patients at high risk of recurrence demonstrated that the vaccine is well tolerated, immunogenic. No grade 4 or 5 toxicities were observed. The only grade 3 response was observed in the nOPT cohort, indicating the increase in peptide dose did not cause any additional toxicity. Given the severity of side effects associated with standard of care chemotherapy for endometrial and ovarian cancer patients, a low toxicity profile is key for any additional therapy given in the adjuvant setting. The E39 vaccine, even given at higher peptide dose, fulfills this requirement.

The data further demonstrate that the E39 vaccine was able to effectively induce a robust immune response. Patients did have a limited DTH response to E39 prior to vaccination, which indicates previous exposure to FBP on the surface of their tumors. The vaccine, however, increased this DTH response in all vaccinated patients and increased the response to an even greater extent in patients receiving the optimal (1.0 mg) dose of the vaccine, reaching statistical significance. The OPT group had a greater increase in DTH from pre- to post-vaccination and the best clinical outcomes.

In the subgroup analysis, optimally dosed patients had an even more pronounced benefit, reaching statistical significance when compared to both the CG and nOPT group. Indeed, it was completely unexpected that patients receiving less than the 1.0 mg OPT dose did not demonstrate a statistically significant benefit when compared to the CG. The OPT group was approximately five times less likely to experience a recurrence when compared to the CG. Clearly, the higher dose of peptide induced a more meaningful response in this group of patients. In addition, the efficacy results indicate that the 1000 mcg dose cohort had increased immune responses and longer disease-free survival rates.

Example 2

Effect of Booster Inoculation on Immune Response

Booster inoculations of peptide vaccines may improve disease-free survival (DFS) (e.g., U.S. Pat. No. 8,222,214), but repeated boosting can theoretically lead to overstimulation and loss of vaccine-induced T cells. Therefore, to assess the use of the attenuated E39' peptide as a booster, E39-vaccinated patients described in Example 1 were randomized to receive either E39 or E39' as a booster to determine the effect on long-term E39-specific immunity. Patients in the VG received six intradermal E39 injections as described in Example 1 as a primary vaccination schedule (PVS). At six months (B1) and at twelve months (B2) after completion of the PVS, patients received either 500 mcg of E39' and 250 mcg GM-CSF or 500 mcg E39 and 250 mcg of GM-CSF as a booster.

Local reactions (LR) were recorded 48-72 hours after each booster. Immune response was determined by measurement of E39 specific CTL levels using a Dextramer reagents in accordance with the manufacturer's instructions (Immudex Limited, Copenhagen, Denmark) as previously described (e.g., Tario et al. Cytometry B Clin. Cytom. 2015; 88B:6-20; Baba J. Transl Med. 2010; 8:84), at R0 (baseline pre-vaccination), RC1 (1 month after completion of PVS), RC6 (6 months after completion of PVS and before booster), RC7 (1 month after booster) and RC12 (6 months after booster and 12 months after completion of PVS). Demographic, safety, immunological, and DFS data were collected and evaluated.

Seventeen patients were included in this portion of the study. For B1, nine patients received E39' and eight patients received E39; and B2 included seven patients in each group (E39 or E39'). There were no significant clinicopathological differences between groups.

The data from a patient receiving E39' as a booster is exemplified in Table 2.

TABLE 2

| | Timepoint | | | | |
|---|---|---|---|---|---|
| | R0 | RC1 | RC6 | RC7 | RC12 |
| E39 CTL Level | 0.018 | 0.018 | 0.078 | .275 | .275 |

An increase in E39-specific CTLs was not seen immediately after completion of the PVS. However, there was a substantial increase by 6 months after completion of the PVS (>4 fold). Even more significantly, the level of CTLS increased even further after boosting with the E39' peptide (>15 fold over baseline) which persisted for at least 6 months.

The average LR for all patients in the E39' vs. E39 groups were 79.7±14.0 mm vs. 82.1±8.3 mm, respectively for B1 (p=0.45) and 74.1±11.5 vs. 78±11.2 mm, respectively for B2 (p=0.41). Clinically, the recurrence rate was 22.2% in the E39' boost group vs. 25% for E39. The estimated 2-year DFS for B1 pts for E39', E39 and the control group (CG) were 66.7%, 58.3%, and 36.0%, respectively; and for B2 pts were 66.7%, 66.7%, and 36.0%, respectively. Comparing just the boosted groups, for B1 the hazard ratio (HR) for E39' vs. E39=0.71 (95% CI: 0.1-5.13), and for B2 the HR for E39' vs. E39=0.82 (95% CI: 0.05-13.24).

The data indicate that the use of an attenuated peptide (E39') booster was safe and as immunogenic as the wildtype peptide (E39) in this randomized trial of optimal boosting strategies. More importantly, the data further show that there appears to be a potential clinical advantage to the use of attenuated E39' peptide booster.

Example 3

Clinical Outcomes and FBP Expression Levels

Disease-free HLA-A2+ patients were vaccinated (VG) and HLA-A2− followed as controls (CG). VG received 6-monthly inoculations of E39+GM-CSF. FBP expression was graded 0-4 based on percentage positive staining; 0-1+ categorized low expression ($FBP_{lo}$), 2-4+ categorized high expression ($FBP_{hi}$). Demographics, FBP expression and disease-free survival (DFS) were analyzed.

Thirty-eight enrolled patients underwent FBP expression testing (CG-n=20; VG-n=18). There were no clinicopathologic differences between groups (p>0.1). Nineteen patients were $FBP_{lo}$ and 19 were $FBP_{hi}$. Median follow up was 16.3 months. In $FBP_{lo}$ patients there was improved DFS in VG (n=8) vs. CG (n=11; 85.7% vs. 17.5%, p=0.01). There was no difference in $FBP_{hi}$ patients (VG:13.9% vs. CG:44.4%, p=0.83). Among $FBP_{lo}$ patients, there was a dose-dependent effect on DFS with patients receiving 1000 mcg having improved DFS vs. <1000 mcg and CG (100% vs. 66.7% vs. 17.5%, p=0.03). (FIGS. 6-10)

Surprisingly, this phase I/IIa revealed a DFS benefit in $FBP_{lo}$, over $FBP_{hi}$ E+OC patients treated with E39. This may be due to immunotolerance in $FBP_{hi}$ patients.

TABLE 3

| | Demographics | | | | | |
|---|---|---|---|---|---|---|
| | | Control | | Treatment | | |
| | | n= | 22 | n= | 29 | |
| Age at enrollment | Median/Range | 61 | 47 | 61 | 37 | 0.754 |
| Race and Ethnicity | Asian | 1 | 4.30% | 1 | 3.40% | |
| | Black | 0 | 0.00% | 1 | 3.40% | |
| | Hispanic | 1 | 4.30% | 1 | 3.40% | |
| | White | 21 | 91.30% | 26 | 89.70% | 0.837 |
| Primary Cancer Site | Endometrial | 4 | 17.40% | 7 | 24.10% | |
| | Ovarian | 19 | 82.60% | 20 | 69.00% | |
| | Peritoneal | 0 | 0.00% | 1 | 3.40% | |
| | Tubal | 0 | 0.00% | 1 | 3.40% | 0.536 |
| FIGO Stage | IA | 3 | 13.00% | 1 | 3.40% | |
| | IB | 1 | 4.30% | 1 | 3.40% | |
| | IC | 0 | 0.00% | 1 | 3.40% | |
| | IIA | 0 | 0.00% | 2 | 6.90% | |
| | IIB | 1 | 4.30% | 0 | 0.00% | |
| | IIC | 3 | 13.00% | 1 | 3.40% | |
| | IIIA | 0 | 0.00% | 1 | 3.40% | |
| | IIIB | 3 | 13.00% | 2 | 6.90% | |
| | IIIC | 7 | 30.40% | 15 | 51.70% | |
| | IV | 4 | 17.40% | 5 | 17.20% | |
| | IVB | 1 | 4.30% | 0 | 0.00% | 0.384 |
| Grade | G1 | 2 | 8.70% | 1 | 3.40% | |
| | G2 | 2 | 8.70% | 2 | 6.90% | |
| | G3 | 19 | 82.60% | 26 | 89.70% | 0.691 |
| | Primary Cancer | 16 | 69.60% | 22 | 75.90% | |
| | Recurrent Cancer | 7 | 30.40% | 7 | 21.40% | 0.661 |

What is claimed is:

1. A method of preventing or reducing a risk of recurrence of ovarian cancer or endometrial cancer in a human subject, which method comprises:
administering to the human subject a peptide vaccine comprising about 1.0 mg of a peptide consisting of the amino acid sequence of SEQ ID NO: 1 and an adjuvant, every 3 to 4 weeks for a period of at least about six months,
wherein the human subject is an HLA-A2+ subject and is in remission following treatment with a standard course of therapy,
wherein the human subject, prior to remission, had ovarian or endometrial cancer cells with low expression of folate receptor-alpha (FRα) or no expression of FRα, wherein low or no expression of FRα is an immunohistochemistry (IHC) rating of 0 or 1 protein expression, and
wherein the method prevents or reduces the risk of recurrence of ovarian cancer or endometrial cancer in the human subject.

2. The method of claim 1, wherein the peptide vaccine is administered by injection.

3. The method of claim 1, wherein the peptide vaccine is administered by intradermal injection.

4. The method of claim 3, wherein the peptide vaccine is administered as split dosages that are administered concurrently.

5. The method of claim 4, wherein the split dosages are administered at one site or at different sites.

6. The method of claim 5, wherein the split dosages are administered at least 5 cm apart.

7. The method of claim 1, wherein the adjuvant is granulocyte macrophage-colony stimulating factor (GM-CSF).

8. The method of claim 7, wherein the peptide vaccine comprises between about 0.01 mg to about 0.5 mg GM-CSF.

9. The method of claim 7, wherein the peptide vaccine comprises about 0.250 mg GM-CSF.

10. The method of claim 1, further comprising administering to the subject a booster composition about six months, or about one year after the primary immunization schedule is completed, wherein the booster composition comprises an effective amount of a peptide consisting of an amino acid sequence selected from the group consisting of SEQ ID NO: 1 and SEQ ID NO: 2, and an adjuvant.

11. The method of claim 10, wherein the peptide in the booster composition consists of the amino acid sequence of SEQ ID NO: 1.

12. The method of claim 10, wherein the peptide in the booster composition consists of the amino acid sequence of SEQ ID NO: 2.

13. The method of claim 10, wherein the booster composition comprises about 0.1 mg to about 2 mg of the peptide.

14. The method of claim 13, wherein the booster composition comprises about 0.5 mg to about 1.0 mg of the peptide.

15. The method of claim 10, wherein the adjuvant in the booster composition is GM-CSF.

16. The method of claim 15, wherein the booster composition comprises about 0.01 mg to about 0.5 mg GM-CSF.

17. The method of claim 16, wherein the booster composition comprises about 0.250 mg GM-CSF.

18. The method of claim 10, wherein the booster composition is administered about six months after the completion of the primary immunization schedule.

19. The method of claim 1, wherein the subject has no evidence of disease (NED).

20. The method of claim 1, wherein the peptide vaccine is administered within about three months after treatment with one or more cancer therapies selected from the group consisting of surgery, radiation, chemotherapy or a combination of one or more thereof.

21. The method of claim 1, wherein the human subject, prior to remission, had ovarian cancer cells with low or no expression of FRα, and wherein the method prevents or reduces a risk of ovarian cancer recurrence.

22. The method of claim 1, wherein the human subject, prior to remission, had endometrial cancer cells with low or no expression of FRα, and wherein the method prevents or reduces a risk of endometrial cancer recurrence.

* * * * *

SEQUENCE LISTING

<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Synthetic: FR-alpha epitope, E39

<400> SEQUENCE: 1

Glu Ile Trp Thr His Ser Tyr Lys Val
1               5

<210> SEQ ID NO 2
<211> LENGTH: 9
<212> TYPE: PRT

<213> ORGANISM: Artificial Sequence
<220> FEATURE:
<223> OTHER INFORMATION: Synthetic: modified FR-alpha epitope, E39'

<400> SEQUENCE: 2

Glu Ile Trp Thr Phe Ser Thr Lys Val
1               5

<210> SEQ ID NO 3
<211> LENGTH: 962
<212> TYPE: DNA
<213> ORGANISM: Artificial Sequence
<220> FEATURE:
<223> OTHER INFORMATION: Synthetic

<400> SEQUENCE: 3

```
tcaaggttaa  acgacaagga  cagacatggc  tcagcggatg  acaacacagc  tgctgctcct    60
tctagtgtgg  gtggctgtag  taggggaggc  tcagacaagg  attgcatggg  ccaggactga   120
gcttctcaat  gtctgcatga  acgccaagca  ccacaaggaa  aagccaggcc  ccgaggacaa   180
gttgcatgag  cagtgtcgac  cctggaggaa  gaatgcctgc  tgttctacca  acaccagcca   240
ggaagcccta  aggatgtttc  ctacctctta  tagattcaac  tggaaccact  gtggagagat   300
ggcacctgcc  tgcaaacggc  atttcatcca  ggacacctgc  tctacgagt  gctcccccaa   360
cttggggccc  tggatccagc  aggtggatca  gagctggcgc  aaagagcggg  tactgaacgt   420
gccccctgtgc  aaagaggact  gtgagcaatg  gtgggaagat  tgtcgcacct  cctacacctg   480
caagagcaac  tggcacaagg  gctggaactg  gacttcaggg  tttaacaagt  gcgcagtggg   540
agctgcctgc  caacctttcc  atttctactt  ccccacaccc  actgttctgt  gcaatgaaat   600
ctggactcac  tcctacaagg  tcagcaacta  cagccgaggg  agtggccgct  gcatccagat   660
gtggttcgac  ccagcccagg  gcaaccccaa  tgaggaggtg  gcgaggttct  atgctgcagc   720
catgagtggg  gctgggccct  gggcagcctg  gccttcctg  cttagcctgg  ccctaatgct   780
gctgtggctg  ctcagctgac  ctccttttac  cttctgatac  ctggaaatcc  ctgccctgtt   840
cagccccaca  gctcccaact  atttggttcc  tgctccatgg  tcgggcctct  gacagccact   900
ttgaataaac  cagacaccgc  acatgtgtct  tgagaattat  ttggaaaaaa  aaaaaaaaa   960
aa                                                                       962
```

<210> SEQ ID NO 4
<211> LENGTH: 257
<212> TYPE: PRT
<213> ORGANISM: Artificial Sequence
<220> FEATURE:
<223> OTHER INFORMATION: Synthetic

<400> SEQUENCE: 4

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys

-continued

```
                        85                      90                      95
Lys Arg His Phe Ile Gln Asp Thr Cys Leu Tyr Glu Cys Ser Pro Asn
            100                     105                 110

Leu Gly Pro Trp Ile Gln Gln Val Asp Gln Ser Trp Arg Lys Glu Arg
        115                     120                 125

Val Leu Asn Val Pro Leu Cys Lys Glu Asp Cys Glu Gln Trp Trp Glu
    130                     135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                     190

Trp Thr His Ser Tyr Lys Val Ser Asn Tyr Ser Arg Gly Ser Gly Arg
        195                     200                 205

Cys Ile Gln Met Trp Phe Asp Pro Ala Gln Gly Asn Pro Asn Glu Glu
    210                     215                 220

Val Ala Arg Phe Tyr Ala Ala Ala Met Ser Gly Ala Gly Pro Trp Ala
225                 230                     235                 240

Ala Trp Pro Phe Leu Leu Ser Leu Ala Leu Met Leu Leu Trp Leu Leu
                245                 250                     255

Ser
```